United States Patent
Hanke et al.

(10) Patent No.: US 7,300,777 B2
(45) Date of Patent: Nov. 27, 2007

(54) FEEDBACK-RESISTANT PYRUVATE CARBOXYLASE GENE FROM CORYNEBACTERIUM

(75) Inventors: Paul D. Hanke, Urbana, IL (US); Anthony J. Sinskey, Boston, MA (US); Laura B. Willis, Cambridge, MA (US); Stephane Guillouet, Ramonville (FR)

(73) Assignees: Archer-Daniels-Midland Company, Decatur, IL (US); Massachusetts Institute of Technology, Cambridge, MA (US)

( * ) Notice: Subject to any disclaimer, the term of this patent is extended or adjusted under 35 U.S.C. 154(b) by 207 days.

(21) Appl. No.: 11/136,887

(22) Filed: May 25, 2005

(65) Prior Publication Data

US 2005/0221452 A1    Oct. 6, 2005

Related U.S. Application Data

(62) Division of application No. 09/974,973, filed on Oct. 12, 2001, now Pat. No. 6,965,021.

(60) Provisional application No. 60/239,913, filed on Oct. 13, 2000.

(51) Int. Cl.
*C12P 13/08* (2006.01)
*C12P 13/24* (2006.01)
*C12P 13/14* (2006.01)
*C12P 13/12* (2006.01)
*C12P 13/10* (2006.01)
*C12P 13/06* (2006.01)
*C07H 21/04* (2006.01)
*C12N 9/00* (2006.01)

(52) U.S. Cl. ............ 435/115; 435/107; 435/110; 435/113; 435/114; 435/116; 435/183; 536/23.2

(58) Field of Classification Search ............ None
See application file for complete search history.

(56) References Cited

U.S. PATENT DOCUMENTS

| 6,171,833 B1 | 1/2001 | Sinskey et al. |
| 6,403,351 B1 | 6/2002 | Sinskey et al. |

FOREIGN PATENT DOCUMENTS

| WO | WO/00/39305 | 7/2000 |

OTHER PUBLICATIONS

PCT/US01/31893—ISR, Aug. 22, 2002, Hanke.
Attwood, P.V., "The Structure and the Mechanism of Action of Pyruvate Carboxylase," Int. J. Biochem. Cell Biol. 27:231-249, Pergamon, Press(1995).
Modak, H.V., and Kelly, D.J. "Acetyl-CoA-dependent pyruvate carboxylase . . . chromatography." Microbiology 141:2619-2628 (1995).
Peters-Wendisch et al. "Pyruvate carboxylase from *Corynebacterium glutamicum*: characterization, expression and inactivation of the pyc gene," Microbiology 144:915-927 (1998).
Koffas et al. (Dec. 24, 1997) GenBank accession AF038548.
Sinskey et al. (Oct. 20, 2000) Database Genseq. accession AABO1436, sequence alignment.

*Primary Examiner*—Elizabeth Slobodyansky
(74) *Attorney, Agent, or Firm*—Buchanan Ingersoll & Rooney PC; Craig G. Cochenour, Esq.; Duane A. Stewart, III, Esq.

(57) ABSTRACT

The present invention relates to a mutated pyruvate carboxylase gene from *Corynebacterium*. The mutant pyruvate carboxylase gene encodes a pyruvate carboxylase enzyme which is resistant to feedback inhibition from aspartic acid. The present invention also relates to a method of replacing the wild-type pyruvate carboxylase gene in *Corynebacterium* with this feedback-resistant pyruvate carboxylase gene. The present invention further relates to methods of the production of amino acids, preferably lysine, comprising the use of this mutant pyruvate carboxylase enzyme in microorganisms.

6 Claims, 12 Drawing Sheets

```
     GTGACTGCTATCACCCTTGGCGGTCTCTTGTTGAAAGGAATAATTACTCTAGTGTCGACT
1    ·········+·········+·········+·········+·········+·········+  60

M  T  A  I  T  L  G  G  L  L  L  K  G  I  I  T  L  V  S  T

CACACATCTTCAACGCTTCCAGCATTCAAAAAGATCTTGGTAGCAAACCGCGGCGAAATC
61   ·········+·········+·········+·········+·········+·········+  120

H  T  S  S  T  L  P  A  F  K  K  I  L  V  A  N  R  G  E  I

GCGGTCCGTGCTTTCCGTGCAGCACTCGAAACCGGTGCAGCCACGGTAGCTATTTACCCC
121  ·········+·········+·········+·········+·········+·········+  180

A  V  R  A  F  R  A  A  L  E  T  G  A  A  T  V  A  I  Y  P

CGTGAAGATCGGGGATCATTCCACCGCTCTTTTGCTTCTGAAGCTGTCCGCATTGGTACT
181  ·········+·········+·········+·········+·········+·········+  240

R  E  D  R  G  S  H  R  S  F  A  S  E  A  V  R  I  G  T

GAAGGCTCACCAGTCAAGGCGTACCTGGACATCGATGAAATTATCGGTGCAGCTAAAAAA
241  ·········+·········+·········+·········+·········+·········+  300

E  G  S  P  V  K  A  Y  L  D  I  D  E  I  I  G  A  A  K  K

GTTAAAGCAGATGCTATTTACCCGGGATATGGCTTCCTGTCTGAAAATGCCCAGCTTGCC
301  ·········+·········+·········+·········+·········+·········+  360

V  K  A  D  A  I  Y  P  G  Y  G  F  L  S  E  N  A  Q  L  A

CGCGAGTGCGCGGAAAACGGCATTACTTTTATTGGCCCAACCCCAGAGGTTCTTGATCTC
361  ·········+·········+·········+·········+·········+·········+  420

R  E  C  A  E  N  G  I  T  F  I  G  P  T  P  E  V  L  D  L

ACCGGTGATAAGTCTCGTGCGGTAACCGCCGCGAAGAAGGCTGGTCTGCCAGTTTTGGCG
421  ·········+·········+·········+·········+·········+·········+  480

T  G  D  K  S  R  A  V  T  A  A  K  K  A  G  L  P  V  L  A

GAATCCACCCCGAGCAAAAACATCGATGACATCGTTAAAAGCGCTGAAGGCCAGACTTAC
481  ·········+·········+·········+·········+·········+·········+  540

```
            CCCATCTTTGTAAAGGCAGTTGCCGGTGGTGGCGGACGCGGTATGCGCTTTGTTTCTTCA
    541     ---------+---------+---------+---------+---------+---------+   600

P  I  F  V  K  A  V  A  G  G  G  R  G  M  R  F  V  S  S

CCTGATGAGCTCCGCAAATTGGCAACAGAAGCATCTCGTGAAGCTGAAGCGGCATTCGGC
    601     ---------+---------+---------+---------+---------+---------+   660

P  D  E  L  R  K  L  A  T  E  A  S  R  E  A  E  A  A  F  G

GACGGTTCGGTATATGTCGAACGTGCTGTGATTAACCCCCAGCACATTGAAGTGCAGATC
    661     ---------+---------+---------+---------+---------+---------+   720

D  G  S  V  Y  V  E  R  A  V  I  N  P  Q  H  I  E  V  Q  I

CTTGGCGATCGCACTGGAGAAGTTGTACACCTTTATGAACGTGACTGCTCACTGCAGCGT
    721     ---------+---------+---------+---------+---------+---------+   780

L  G  D  R  T  G  E  V  V  H  L  Y  E  R  D  C  S  L  Q  R

CGTCACCAAAAAGTTGTCGAAATTGCGCCAGCACAGCATTTGGATCCAGAACTGCGTGAT
    781     ---------+---------+---------+---------+---------+---------+   840

R  H  Q  K  V  V  E  I  A  P  A  Q  H  L  D  P  E  L  R  D

CGCATTTGTGCGGATGCAGTAAAGTTCTGCCGCTCCATTGGTTACCAGGGCGCGGGAACC
    841     ---------+---------+---------+---------+---------+---------+   900

R  I  C  A  D  A  V  K  F  C  R  S  I  G  Y  Q  G  A  G  T

GTGGAATTCTTGGTCGATGAAAAGGGCAACCACGTTTTCATCGAAATGAACCCACGTATC
    901     ---------+---------+---------+---------+---------+---------+   960

V  E  F  L  V  D  E  K  G  N  H  V  F  I  E  M  N  P  R  I

CAGGTTGAGCACACCGTGACTGAAGAAGTCACCGAGGTGGACCTGGTGAAGGCGCAGATG
    961     ---------+---------+---------+---------+---------+---------+  1020

Q  V  E  H  T  V  T  E  E  V  T  E  V  D  L  V  K  A  Q  M

CGCTTGGCTGCTGGTGCAACCTTGAAGGAATTGGGTCTGACCCAAGATAAGATCAAGACC
   1021     ---------+---------+---------+---------+---------+---------+  1080

```
            CACGGTGCAGCACTGCAGTGCCGCATCACCACGGAAGATCCAAACAACGGCTTCCGCCCA
1081  ·········+·········+·········+·········+·········+·········+ 1140

H  G  A  A  L  Q  C  R  I  T  T  E  D  P  N  N  G  F  R  P

GATACCGGAACTATCACCGCGTACCGCTCACCAGGCGGAGCTGGCGTTCGTCTTGACGGT
1141  ·········+·········+·········+·········+·········+·········+ 1200

D  T  G  T  I  T  A  Y  R  S  P  G  G  A  G  V  R  L  D  G

GCAGCTCAGCTCGGTGGCGAAATCACCGCACACTTTGACTCCATGCTGGTGAAAATGACC
1201  ·········+·········+·········+·········+·········+·········+ 1260

A  A  Q  L  G  G  E  I  T  A  H  F  D  S  M  L  V  K  M  T

TGCCGTGGTTCCGACTTTGAAACTGCTGTTGCTCGTGCACAGCGCGCGTTGGCTGAGTTC
1261  ·········+·········+·········+·········+·········+·········+ 1320

C  R  G  S  D  F  E  T  A  V  A  R  A  Q  R  A  L  A  E  F

ACCGTGTCTGGTGTTGCAACCAACATTGGTTTCTTGCGTGCGTTGCTGCGGGAAGAGGAC
1321  ·········+·········+·········+·········+·········+·········+ 1380

T  V  S  G  V  A  T  N  I  G  F  L  R  A  L  L  R  E  E  D

TTCACTTCCAAGCGCATCGCCACCGGATTTATCGGCGATCACCCACACCTCCTTCAGGCT
1381  ·········+·········+·········+·········+·········+·········+ 1440

F  T  S  K  R  I  A  T  G  F  I  G  D  H  P  H  L  L  Q  A

CCACCTGCGGATGATGAGCAGGGACGCATCCTGGATTACTTGGCAGATGTCACCGTGAAC
1441  ·········+·········+·········+·········+·········+·········+ 1500

P  P  A  D  D  E  Q  G  R  I  L  D  Y  L  A  D  V  T  V  N

AAGCCTCATGGTGTGCGTCCAAAGGATGTTGCAGCACCAATCGATAAGCTGCCCAACATC
1501  ·········+·········+·········+·········+·········+·········+ 1560

K  P  H  G  V  R  P  K  D  V  A  A  P  I  D  K  L  P  N  I

AAGGATCTGCCACTGCCACGCGGTTCCCGTGACCGCCTGAAGCAGCTTGGCCCAGCCGCG
1561  ·········+·········+·········+·········+·········+·········+ 1620

```
         TTTGCTCGTGATCTCCGTGAGCAGGACGCACTGGCAGTTACTGATACCACCTTCCGCGAT
   1621  ----------+---------+---------+---------+---------+---------+  1680

F   A   R   D   L   R   E   Q   D   A   L   A   V   T   D   T   T   F   R   D

GCACACCAGTCTTTGCTTGCGACCCGAGTCCGCTCATTCGCACTGAAGCCTGCGGCAGAG
   1681  ----------+---------+---------+---------+---------+---------+  1740

A   H   Q   S   L   L   A   T   R   V   R   S   F   A   L   K   P   A   A   E

GCCGTCGCAAAGCTGACTCCTGAGCTTTTGTCCGTGGAGGCCTGGGGCGGCGCGACCTAC
   1741  ----------+---------+---------+---------+---------+---------+  1800

A   V   A   K   L   T   P   E   L   L   S   V   E   A   W   G   G   A   T   Y

GATGTGGCGATGCGTTTCCTCTTTGAGGATCCGTGGGACAGGCTCGACGAGCTGCGCGAG
   1801  ----------+---------+---------+---------+---------+---------+  1860

D   V   A   M   R   F   L   F   E   D   P   W   D   R   L   D   E   L   R   E

GCGATGCCGAATGTAAACATTCAGATGCTGCTTCGCGGCCGCAACACCGTGGGATACACC
   1861  ----------+---------+---------+---------+---------+---------+  1920

A   M   P   N   V   N   I   Q   M   L   L   R   G   R   N   T   V   G   Y   T

CCGTACCCAGACTCCGTCTGCCGCGCGTTTGTTAAGGAAGCTGCCAGCTCCGGCGTGGAC
   1921  ----------+---------+---------+---------+---------+---------+  1980

P   Y   P   D   S   V   C   R   A   F   V   K   E   A   A   S   S   G   V   D

ATCTTCCGCATCTTCGACGCGCTTAACGACGTCTCCCAGATGCGTCCAGCAATCGACGCA
   1981  ----------+---------+---------+---------+---------+---------+  2040

I   F   R   I   F   D   A   L   N   D   V   S   Q   M   R   P   A   I   D   A

GTCCTGGAGACCAACACCGCGGTAGCCGAGGTGGCTATGGCTTATTCTGGTGATCTCTCT
   2041  ----------+---------+---------+---------+---------+---------+  2100

V   L   E   T   N   T   A   V   A   E   V   A   M   A   Y   S   G   D   L   S

GATCCAAATGAAAAGCTCTACACCCTGGATTACTACCTAAAGATGGCAGAGGAGATCGTC
   2101  ----------+---------+---------+---------+---------+---------+  2160

```
       AAGTCTGGCGCTCACATTCTGGCCATTAAGGATATGGCTGGTCTGCTTCGCCCAGCTGCG
2161   ---------+---------+---------+---------+---------+---------+ 2220

K  S  G  A  H  I  L  A  I  K  D  M  A  G  L  L  R  P  A  A

GTAACCAAGCTGGTCACCGCACTGCGCCGTGAATTCGATCTGCCAGTGCACGTGCACACC
2221   ---------+---------+---------+---------+---------+---------+ 2280

V  T  K  L  V  T  A  L  R  R  E  F  D  L  P  V  H  V  H  T

CACGACACTGCGGGTGGCCAGTTGGCTACCTACTTTGCTGCAGCTCAAGCTGGTGCAGAT
2281   ---------+---------+---------+---------+---------+---------+ 2340

H  D  T  A  G  G  Q  L  A  T  Y  F  A  A  A  Q  A  G  A  D

GCTGTTGACGGTGCTTCCGCACCACTGTCTGGCACCACCTCCCAGCCATCCCTGTCTGCC
2341   ---------+---------+---------+---------+---------+---------+ 2400

A  V  D  G  A  S  A  P  L  S  G  T  T  S  Q  P  S  L  S  A

ATTGTTGCTGCATTCGCGCACACCCGTCGCGATACCGGTTTGAGCCTCGAGGCTGTTTCT
2401   ---------+---------+---------+---------+---------+---------+ 2460

I  V  A  A  F  A  H  T  R  R  D  T  G  L  S  L  E  A  V  S

GACCTCGAGCCGTACTGGGAAGCTGTGCGCGGACTGTACCTGCCATTTGAGTCTGGAACC
2461   ---------+---------+---------+---------+---------+---------+ 2520

D  L  E  P  Y  W  E  A  V  R  G  L  Y  L  P  F  E  S  G  T

CCAGGCCCAACCGGTCGCGTCTACCGCCACGAAATCCCAGGCGGACAGTTGTCCAACCTG
2521   ---------+---------+---------+---------+---------+---------+ 2580

P  G  P  T  G  R  V  Y  R  H  E  I  P  G  G  Q  L  S  N  L

CGTGCACAGGCCACCGCACTGGGCCTTGCTGATCGCTTCGAGCTCATCGAAGACAACTAC
2581   ---------+---------+---------+---------+---------+---------+ 2640

R  A  Q  A  T  A  L  G  L  A  D  R  F  E  L  I  E  D  N  Y

GCAGCCGTTAATGAGATGCTGGGACGCCCAACCAAGGTCACCCCATCCTCCAAGGTTGTT
2641   ---------+---------+---------+---------+---------+---------+ 2700

```
            GGCGACCTCGCACTCCACCTGGTTGGTGCGGGTGTAGATCCAGCAGACTTTGCTGCAGAC
     2701   ---------+---------+---------+---------+---------+---------+  2760

G  D  L  A  L  H  L  V  G  A  G  V  D  P  A  D  F  A  A  D

CCACAAAAGTACGACATCCCAGACTCTGTCATCGCGTTCCTGCGCGGCGAGCTTGGTAAC
     2761   ---------+---------+---------+---------+---------+---------+  2820

P  Q  K  Y  D  I  P  D  S  V  I  A  F  L  R  G  E  L  G  N

CCTCCAGGTGGCTGGCCAGAACCACTGCGCACCCGCGCACTGGAAGGCCGCTCCGAAGGC
     2821   ---------+---------+---------+---------+---------+---------+  2880

P  P  G  W  P  E  P  L  R  T  R  A  L  E  G  R  S  E  G

AAGGCACCTCTGACGGAAGTTCCTGAGGAAGAGCAGGCGCACCTCGACGCTGATGATTCC
     2881   ---------+---------+---------+---------+---------+---------+  2940

K  A  P  L  T  E  V  P  E  E  E  A  H  L  D  A  D  D  S

AAGGAACGTCGCAACAGCCTCAACCGCCTGCTGTTCCCGAAGCCAACCGAAGAGTTCCTC
     2941   ---------+---------+---------+---------+---------+---------+  3000

K  E  R  R  N  S  L  N  R  L  L  F  P  K  P  T  E  E  F  L

GAGCACCGTCGCCGCTTCGGCAACACCTCTGCGCTGGATGATCGTGAATTCTTCTACGGA
     3001   ---------+---------+---------+---------+---------+---------+  3060

E  H  R  R  R  F  G  N  T  S  A  L  D  D  R  E  F  F  Y  G

CTGGTCGAGGGCCGCGAGACTTTGATCCGCCTGCCAGATGTGCGCACCCCACTGCTTGTT
     3061   ---------+---------+---------+---------+---------+---------+  3120

L  V  E  G  R  E  T  L  I  R  L  P  K  V  R  T  P  L  L  V

CGCCTGGATGCGATCTCTGAGCCAGACGATAAGGGTATGCGCAATGTTGTGGCCAACGTC
     3121   ---------+---------+---------+---------+---------+---------+  3180

R  L  D  A  I  S  E  P  D  D  K  G  M  R  N  V  V  A  N  V

AACGGCCAGATCCGCCCAATGCGTGTGCGTGACCGCTCCGTTGAGTCTGTCACCGCAACC
     3181   ---------+---------+---------+---------+---------+---------+  3240

```
      GCAGAAAAGGCAGATTCCTCCAACAAGGGCCATGTTGCTGCACCATTCGCTGGTGTTGTC
3241  ---------+---------+---------+---------+---------+---------+ 3300

A  E  K  A  D  S  S  N  K  G  H  V  A  A  P  F  A  G  V  V

ACTGTGACTGTTGCTGAAGGTGATGAGGTCAAGGCTGGAGATGCAGTCGCAATCATCGAG
3301  ---------+---------+---------+---------+---------+---------+ 3360

T  V  T  V  A  E  G  D  E  V  K  A  G  D  A  V  A  I  I  E

GCTATGAAGATGGAAGCAACAATCACTGCTTCTGTTGACGGCAAGATTGAACGCGTTGTG
3361  ---------+---------+---------+---------+---------+---------+ 3300

A  M  K  M  E  A  T  I  T  A  S  V  D  G  K  I  E  R  V  V
      GTTCCTGCTGCAACGAAGGTGGAAGGTGGCGACTTGATCGTCGTCGTTTCCTAA
3421  ---------+---------+---------+---------+---------+---- 3474

|            |                   | 10         | 20         | 30         | 40         |
|            |                   |            |            |            |            |

ATCC 21523                 MSTHTSSTLPAFKKILVANRGEIAVRAFRAALETGAATVAIYP
NRRL-B11474   MTAITLGGLLLKGIITLV 50          60          70          80          90         100
ATCC 21523    REDRGSFHRSFASEAVRIGTEGSPVKAYLDIDEIIGAAKKVKADAIYPGYGFLSENAQLA
NRRL-B11474

110         120         130         140         150         160
ATCC 21523    RECAENGITFIGPTPEVLDLTGDKSRAVTAAKKAGLPVLAESTPSKNIDEIVKSAEGQTY
NRRL-B11474                                                    D 170         180         190         200         210         220
ATCC 21523    PIFVKAVAGGGGRGMRFVASPDELRKLATEASREAEAAFGDGAVYVERAVINPQHIEVQI
NRRL-B11474                S                                  S 230         240         250         260         270         280
ATCC 21523    LGDHTGEVVHLYERDCSLQRRHQKVVEIAPAAQHLDPELRDRICADAVKFCRSIGYQGAG
NRRL-B11474    R 290         300         310         320         330         340
ATCC 21523    VEFLVDEKGNHVFIEMNPRIQVEHTVTEEVTEVDLVKAQMRLAAGATLKELGLTQDKIKT
NRRL-B11474

350         360         370         380         390         400
ATCC 21523    HGAALQCRITTEDPNNGFRPDTGTITAYRSPGGAGVRLDGAAQLGGEITAHFDSMLVKMT
NRRL-B11474

410         420         430         440         450         460
ATCC 21523    CRGSDFETAVARAQRALAEFTVSGVATNIGFLRALLREEDFTSKRIATGFIADHPHLLQA
NRRL-B11474                                                               G 470         480         490         500         510         520
ATCC 21523    PPADDEQGRILDYLADVTVNKPHGVRPKDVAAPIDKLPNIKDLPLPRGSRDRLKQLGPAA
NRRL-B11474

530         540         550         560         570         580
ATCC 21523    FARDLREQDALAVTDTTFRDAHQSLLATRVRSFALKPAAEAVAKLTPELLSVEAWGGATY
NRRL-B11474

590         600         610         620         630         640
ATCC 21523    DVAMRFLFEDPWDRLDELREAMPNVNIQMLLRGRNTVGYTPYPDSVCRAFVKEAASSGVD
NRRL-B11474

650         660         670         680         690         700
ATCC 21523    IFRIFDALNDVSQMRPAIDAVLETNTAVAEVAMAYSGDLSDPNEKLYTLDYYLKMAEEIV
NRRL-B11474

710         720         730         740         750         760
ATCC 21523    KSGAHILAIKDMAGLLRPAAVTKLVTALRREFDLPVHVHTHDTAGGQLATYFAAAQAGAD
NRRL-B11474

770         780         790         800         810         820
ATCC 21523    AVDGASAPLSGTTSQPSLSAIVAAFAHTRRDTGLSLEAVSDLEPYWEAVRGLYLPFESGT
NRRL-B11474

FIG. 2A

|  | 830 | 840 | 850 | 860 | 870 | 880 |
|---|---|---|---|---|---|---|
ATCC 21523  
NRRL-B11474

PGPTGRVYRHEIPGGQLSNLRAQATALGLADRFELIEDNYAAVNEMLGRPTKVTPSSKVV

|  | 890 | 900 | 910 | 920 | 930 | 940 |

ATCC 21523  
NRRL-B11474

GDLALHLVGAGVDPADFAADPQKYDIPDSVIAFLRGELGNPPGGWPEPLRTRALEGRSEG

|  | 950 | 960 | 970 | 980 | 990 | 1000 |

ATCC 21523  
NRRL-B11474

KAPLTEVPEEEQAHLDADDSKERRNSLNRLLFPKPTEEFLEHRRRFGNTSALDDREFFYG

|  | 1010 | 1020 | 1030 | 1040 | 1050 | 1060 |

ATCC 21523  
NRRL-B11474

LVEGRETLIRLPDVRTPLLVRLDAISEPDDKGMRNVVANVNGQIRPMRVRDRSVESVTAT

|  | 1070 | 1080 | 1090 | 1100 | 1110 | 1120 |

ATCC 21523  
NRRL-B11474

AEKADSSNKGHVAAPFAGVVTVTVAEGDEVKAGDAVAIIEAMKMEATITASVDGKIDRVV  
                                                                                                                                                                                             E

|  | 1130 | 1140 |

ATCC 21523  
NRRL-B11474

VPAATKVEGGDLIVVVS

FIG. 2B

FEEDBACK-RESISTANT PYRUVATE CARBOXYLASE GENE FROM CORYNEBACTERIUM

CROSS-REFERENCE TO RELATED APPLICATIONS

This application is a divisional application that claims the benefit of priority of U.S. patent application Ser. No. 09/974,973, filed on Oct. 12, 2001, now U.S. Pat. No. 6,965,021, and claims the benefit of priority of U.S. Provisional Patent Application No. 60/239,913, filed on Oct. 13, 2000, both of which are incorporated herein by reference in their entirety.

BACKGROUND OF THE INVENTION

1. Field of the Invention

The present invention relates to a mutated pyruvate carboxylase gene from *Corynebacterium*. The mutant pyruvate carboxylase gene encodes a pyruvate carboxylase enzyme which is resistant to feedback inhibition from aspartic acid. The present invention also relates to a method of replacing the wild-type pyruvate carboxylase gene in *Corynebacterium* with this feedback-resistant pyruvate carboxylase gene. The present invention further relates to methods of the production of amino acids, preferably lysine, comprising the use of this mutant pyruvate carboxylase enzyme in microorganisms.

2. Background Art

Pyruvate carboxylase is an important biotin-containing enzyme found in a variety of plants and animals, as well as some groups of bacteria (Nodak, H. V. and Kelly, D. J., Microbiology 141:2619-2628 (1995)). In the presence of adenosine triphosphate (ATP) and magnesium ions, pyruvate carboxylase catalyzes the two-step carboxylation of pyruvate to form oxaloacetate, as shown in the equations below:

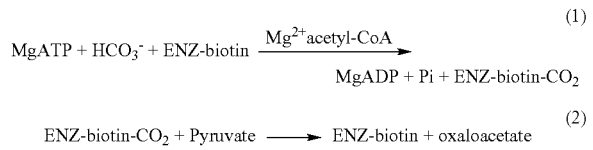

In reaction (1) the ATP-dependent biotin carboxylase domain carboxylates a biotin prosthetic group linked to a specific lysine residue in the biotin-carboxyl-carrier protein (BCCP) domain. Acetyl-coenzyme A activates reaction (1) by increasing the rate of bicarbonate-dependent ATP cleavage. In reaction (2), the BCCP domain donates the $CO_2$ to pyruvate in a reaction catalyzed by the transcarboxylase domain (Attwood, P. V., *Int. J. Biochem. Cell. Biol.* 27:231-249 (1995)).

In bacteria such as *Corynebacterium glutamicum*, pyruvate carboxylase is utilized during carbohydrate metabolism to form oxaloacetate, which is in turn used in the biosynthesis of amino acids, particularly L-lysine and L-glutamate. Furthermore, in response to a cell's metabolic needs and internal environment, the activity of pyruvate carboxylase is subject to both positive and negative feedback mechanisms, where the enzyme is activated by acetyl-CoA, and inhibited by aspartic acid. Based on its role in the pathway of amino acid synthesis, and its ability to be regulated, pyruvate carboxylase plays a vital role in the synthesis of amino acids.

Bacteria such as *C. glutamicum* and *E. coli* are widely used in industry for the production of amino acids such as L-glutamate and L-lysine. Because of the central importance of pyruvate carboxylase in the production of amino acids, particularly L-glutamate and L-lysine, the exploitation of pyruvate carboxylase to increase amino acid production is of great interest in an industrial setting. Thus, promoting the positive feedback mechanism of pyruvate carboxylase, or inhibiting its negative feedback mechanism, in *C. glutamicum* or could augment amino acid production on an industrial scale.

BRIEF SUMMARY OF THE INVENTION

One aspect of the present invention relates to a nucleic acid molecule comprising a nucleotide sequence which codes for a pyruvate carboxylase of SEQ ID NO:19, wherein this pyruvate carboxylase contains at least one mutation which desensitizes the pyruvate carboxylase to feedback inhibition by aspartic acid.

Another aspect of the present invention provides methods for using the nucleic acid of SEQ ID NO: 1, which encodes the amino acid sequence of a mutant pyruvate carboxylase. Such uses include the replacement of the wild-type pyruvate carboxylase with the feedback-resistant pyruvate carboxylase, and the production of amino acids. An additional aspect of the present invention provides a polypeptide comprising the amino acid sequence of SEQ ID NO:2. Still another aspect of the present invention provides a polypeptide comprising the amino acid sequence selected from the group comprising SEQ ID NO: 6, SEQ ID NO: 8, SEQ ID NO: 10, SEQ ID NO: 12 SEQ ID NO: 14, SEQ ID NO: 16 and SEQ ID NO: 18.

Another aspect of the present invention also relates to a nucleic acid molecule comprising a nucleotide sequence which encodes the amino acid sequence of SEQ ID NO: 2 or the amino acid sequence encoded by the DNA contained in Deposit Number NRRL B-11474. Another aspect of the present invention further relates to a nucleic acid molecule comprising the nucleotide sequence of SEQ ID NO: 1.

BRIEF DESCRIPTION OF THE DRAWINGS/FIGURES

FIGS. 1A-1G show the full-length nucleotide sequence (SEQ ID NO:1) encoding the amino acid sequence of feedback-resistant pyruvate carboxylase, and the corresponding amino acid sequence (SEQ ID NO:2).

FIG. 2 shows the amino acid sequence of the wild-type pyruvate carboxylase (SEQ ID NO: 19), isolated from *Corynebacterium glutamicum* ATCC 21253. The specific changes corresponding to the amino acid sequence of the feedback-resistant pyruvate carboxylase (SEQ ID NO: 2) ISOLATED FROM *Corynebacterium glutamicum* NRRL B-1474, are indicated.

DETAILED DESCRIPTION OF THE INVENTION

Figure 3A:
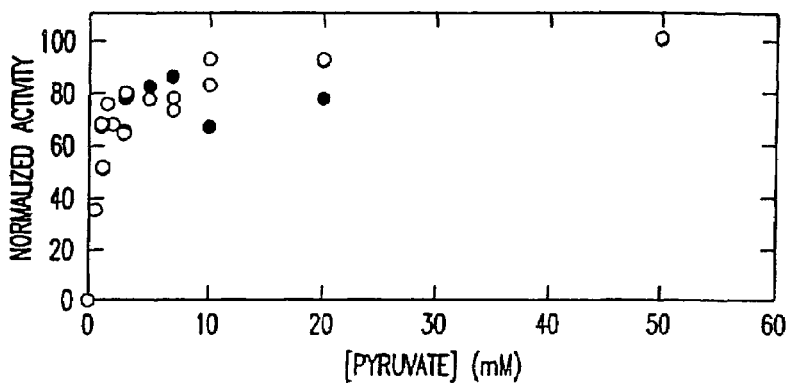
FIG. 3 shows the effects of various substrate concentrations on the pyruvate carboxylase activity in *C. glutamicum* ATCC 21253 and NRRL B-1474.

The present invention relates to variations of the polypeptide comprising the amino acid sequence which codes for the pyruvate carboxylase as shown in SEQ ID NO:19. Preferably, the variations of pyruvate carboxylase enzyme in the present invention contain at least one mutation which desensitizes the pyruvate carboxylase to feedback inhibition by aspartic acid. Such mutations may include deletions, insertions, inversions, repeats, and type substitutions. More preferably, the amino acid sequence mutation which desensitizes the wild-type pyruvate carboxylase enzyme (SEQ ID NO:19) to feedback inhibition comprises at least one substitution selected from the group consisting of (a) methionine at position 1 being replaced with a valine, (b) glutamic acid at position 153 being replaced with an aspartic acid, (c) alanine at position 182 being replaced with a serine, (d) alanine at position 206 being replaced with a serine, (e) histidine at position 227 being replaced with an arginine, (f) alanine at position 452 being replaced with a glycine, and (g) aspartic acid at position 1120 being replaced with a glutamic acid. Still more preferably, the variation of the polypeptide encoded by the amino acid sequence of SEQ ID NO:19 contains more than one of the above-mentioned mutations. Most preferably, the variation of the polypeptide encoded by the amino acid sequence of SEQ ID NO:19 contains all of the above-mentioned mutations. As one of ordinary skill in the art would appreciate, the numbering of amino acid residues of a protein as used herein, begins at the amino terminus (N-terminus) and proceeds towards the carboxy terminus (C-terminus), such that the first amino acid at the N-terminus is position 1.

An embodiment of the present invention relates to an isolated or purified nucleic acid molecule comprising a nucleotide sequence selected from the group consisting of: (a) a nucleotide sequence which encodes the amino acid sequence of SEQ ID NO: 2; (b) a nucleotide sequence encoding the amino acid sequence encoded by the DNA contained in Deposit Number NRRL B-11474 or; (c) a nucleotide sequence complementary to any of the nucleotide sequences in (a) or (b).

Further embodiments of the invention include isolated nucleic acid molecules that comprise a polynucleotide having a nucleotide sequence at least 90% identical, and more preferably at least 95%, 97%, 98%, 99% or 100% identical, to any of the nucleotide sequences in (a), (b), (c) or (d) above, or a polynucleotide which hybridizes under stringent hybridization conditions to a polynucleotide having a nucleotide sequence identical to a nucleotide sequence in (a), (b), (c) or (d) above. However, the polynucleotide which hybridizes does not hybridize under stringent hybridization conditions to a polynucleotide having a nucleotide sequence consisting of only A residues or of only T residues.

Another aspect of the invention is directed to nucleic acid molecules at least 90%, 95%, 97%, 98% or 99% identical to the nucleic acid sequence shown in FIG. 1 (SEQ ID NO: 1), or to the nucleic acid sequence of the deposited DNA (NRRL B-30293, deposited May 12, 2000).

A further aspect of the invention provides a nucleic acid molecule comprising a nucleotide sequence selected from the group consisting of: SEQ ID NO:5, SEQ ID NO:7, SEQ ID NO:9, SEQ ID NO:11, SEQ ID NO:13, SEQ ID NO:15 and SEQ ID NO:17.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence encoding the pyruvate carboxylase polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequence shown in FIG. 1 or to the nucleotide sequence of the deposited DNA can be determined conventionally using known computer programs such as the FastA program. FastA performs a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

Unless otherwise indicated, all nucleotide sequences determined by sequencing a DNA molecule herein were determined using an automated DNA sequencer (such as the ABI Prism 377). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, DNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In another aspect, the invention provides an isolated nucleic acid molecule comprising a polynucleotide which hybridizes under stringent hybridization conditions to a portion of the polynucleotide in a nucleic acid molecule of the invention described herein. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's-solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers.

Of course, polynucleotides hybridizing to a larger portion of the reference polynucleotide (e.g., the deposited plasmid), for instance, a portion 25-750 nt in length, or even to the entire length of the reference polynucleotide, are also useful as probes according to the present invention, as are polynucleotides corresponding to most, if not all, of the nucleotide sequences of any of the nucleotide sequences included in the present intention. By a portion of a polynucleotide of "at least 20 nt in length," for example, is intended 20 or more contiguous nucleotides from any of the nucleotide sequences of the reference polynucleotides, (e.g., the deposited DNA or the nucleotide sequence as shown in any of the figures). As indicated, such portions are useful diagnostically either as a probe, according to conventional DNA hybridization techniques, or as primers for amplification of a target sequence by the polymerase chain reaction (PCR), as described, for instance, in *Molecular Cloning, A Laboratory Manual*, 2nd. edition, edited by Sambrook, J., Fritsch, E. F. and Maniatis, T., (1989), Cold Spring Harbor Laboratory Press, the entire disclosure of which is hereby incorporated herein by reference.

The nucleic acid molecules of the present invention are suitable for use in vectors. As such, polynucleotides of interest can be joined to the nucleic acid molecules of the present invention, which may optionally contain selectable markers. A preferred embodiment of the present invention is that the vector comprises a functional *Corynebacterium* replication origin. A replication origin is a nucleotide sequence, typically several hundred base pairs long, that is vital to the initiation of DNA replication.

The vectors can optionally contain an exogenous terminator of transcription; an exogenous promoter; and a discrete series of restriction endonuclease recognition sites, said series being between said promoter and said terminator. The vector can optionally contain their native expression vectors and/or expression vectors which include chromosomal-, and episomal-derived vectors, e.g., vectors derived from bacterial exogenous plasmids, bacteriophage, and vectors derived from combinations thereof, such as cosmids and phagemids.

A DNA insert of interest should be operatively linked to an appropriate promoter, such as its native promoter or a host-derived promoter, the phage lambda $P_L$ promoter, the phage lambda $P_R$ promoter, the *E. coli* lac promoters, such as the lacI and lacZ promoters, trp and tac promoters, the T3 and T7 promoters and the gpt promoter to name a few. Other suitable promoters will be known to the skilled artisan.

The expression constructs will further contain sites for transcription initiation, termination and, in the transcribed region, a ribosome binding site for translation. The coding portion of the mature transcripts expressed by the constructs can include a translation initiating codon at the beginning and a termination codon appropriately positioned at the end of the polypeptide to be translated.

As indicated, the expression vectors will preferably include at least one selectable marker. Preferably the selection marker comprises a nucleotide sequence which confers antibiotic resistance in a host cell population. Such markers include amikacin, augmentin (amoxicillin plus clavulonic acid), ampicillin, cefazolin, cefoxitin, ceftazidime, ceftiofur, cephalothin, enrofloxacin, florfenicol, gentamicin, imipenem, kanamycin, penicillin, sarafloxicin, spectinomycin, streptomycin, tetracycline, ticarcillin, tilmicosin, or chloramphenicol resistance genes. Other suitable markers will be readily apparent to the skilled artisan.

The invention also provides for a method of producing a host cell where the expression vectors of the current invention have been introduced into the host cell. Methods of introducing genetic material into host cells, such as those described in typical molecular biology laboratory manuals, for example J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989), are well known to the skilled artisan. These methods include, but are not limited to, calcium phosphate transfection, DEAE-dextran mediated transfection, microinjection, lipid-mediated transfection, electroporation or infection. Accordingly, a preferred embodiment of the present invention provides a host cell comprising the vector of the present invention.

As used in the present invention, a host cell refers to any prokaryotic or eukaryotic cell where the desired nucleic acid sequence has been introduced into the cell. There are a variety of suitable host cells, including but not limited to bacterial, fungal, insect, mammalian and plant cells, that can be utilized in the present invention. Representative bacterial-host cells include, but are not limited to, *Streptococci, Staphylococci, E. coli, Streptomyces, Bacillus* and *Corynebacterium*. Representative fungal cells include but are not limited to, yeast cells and *Aspergillus*. Insect cells include, but are not limited to, *Drosophila* S2 and *Spodoptera* Sf9 cells. Examples of mammalian cells include, but are not limited to, CHO, COS and Hela cells.

The present invention provides methods for utilizing the nucleic acid of SEQ ID NO: 1, which encodes the amino acid sequence of a mutant pyruvate carboxylase. Such methods include the replacement of the wild-type pyruvate carboxylase with the feedback-resistant pyruvate carboxylase, and the production of amino acids. The method for replacement of a wild-type pyruvate carboxylase gene, with a feedback resistant pyruvate carboxylase gene, in a *Corynebacterium glutamicum* host cell comprises the steps of: (a) replacing a genomic copy of the wild-type pyruvate carboxylase gene with a selectable marker gene through homologous recombination to form a first recombinant strain; and (b) replacing the selectable marker gene of step (a) in the first recombinant strain, with the feedback resistant pyruvate carboxylase gene through homologous recombination to form a second recombinant strain. The homologous recombination in steps (a) and (b) would occur between the genetic material of the host cell and any of the vectors of the present invention.

Homologous recombination is a technique that is used to disrupt endogenous nucleotide sequences in a host cell. Normally, when an exogenous nucleotide sequence is inserted into a host cell, this polynucleotide may randomly insert into any area of the host cell's genome, including endogenous plasmids. However, with homologous recombination, the exogenous nucleotide sequence contains sequences that are homologous to an endogenous nucleotide sequence within the host cell. Once introduced into the cell, for example by electroporation, the exogenous nucleotide sequence will preferentially recombine with and replace the endogenous nucleotide sequence with which it is homologous.

As used herein, an exogenous nucleotide sequence, is a nucleotide sequence which is not found in the host cell. Thus, the term exogenous nucleotide sequence is meant to encompass a nucleotide sequence that is foreign to the host cell, as well as a nucleotide sequence endogenous, or native, to the host cell that has been modified. Modification of the endogenous nucleotide sequence may include, for instance, mutation of the native nucleotide sequence or any of its regulatory elements. As used herein, mutation is defined as any change in the wild-type sequence of the host's genetic material, including plasmid DNA. An additional form of modification may also include fusion of the endogenous nucleotide sequence to a nucleotide sequence that is normally not present, in relation to the endogenous nucleotide sequence.

Host cells that have undergone homologous recombination are selected on the basis of antibiotic resistance through the use of, for example, the selectable markers mentioned above. The process of selecting cells that have undergone homologous recombination will be readily apparent to one skilled in the art.

Another aspect of the current invention is a method for producing amino acids. In the current context, production of amino acids is accomplished by culturing host cells where a vector of the present invention has been introduced into the host cell, or culturing host cells where homologous recombination, involving a vector of the present invention, has taken place. Culturing of the host cells is performed in the appropriate culture media. Subsequent to culturing the host cells in culture media, the desired amino acids are separated from the culture media. Preferably, the amino acids produced by the methods described herein include L-lysine, L-threonine, L-methionine, L-isoleucine, L-glutamate, L-arginine and L-proline. More preferably, the present invention relates to the production of L-lysine.

The present invention provides an isolated or purified polypeptide encoded by the DNA plasmid encoding pyruvate carboxylase contained in Deposit Number NRRL B-30293, or the amino acid sequence of SEQ ID NO: 2. Still another aspect of the present invention provides a polypeptide comprising the amino acid sequence selected from the group consisting of SEQ ID NO: 6, SEQ ID NO: 8, SEQ ID NO: 10, SEQ ID NO: 12, SEQ ID NO: 14, SEQ ID NO: 16 and SEQ ID NO: 18.

Accordingly, SEQ ID NO: 6 corresponds to the amino acid sequence: PSKNIDDIVKSAE. SEQ ID NO:8 corresponds to the amino acid sequence: RGMRFVSSPDELR. SEQ ID NO: 10 corresponds to the amino acid sequence: AAFGDGSVYVERA. SEQ ID NO: 12 corresponds to the amino acid sequence: VQILGDRTGEVVH. SEQ ID NO: 14 corresponds to the amino acid sequence: IATGFIGDH-PHLL. SEQ ID NO: 16 corresponds to the amino acid sequence: TITASYDGKIERV. SEQ ID NO: 18 corresponds to the amino acid sequence: MTAITLGGLLLKGIITLV.

All of the polypeptides of the present invention are preferably provided in an isolated form. As used herein, "isolated polypeptide" is intended to mean a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host. For example, a recombinantly produced version of the pyruvate carboxylase enzyme can be substantially purified by the one-step method described in Smith and Johnson, *Gene* 67:3140 (1988).

One aspect of the present invention include the polypeptides which are at least 80% identical, more preferably at least 90%, 95% or 100% identical to the polypeptide encoded by the DNA plasmid encoding pyruvate carboxylase contained in Deposit Number NRRL B-30293, the polypeptide of SEQ ID NO: 2.

By a polypeptide having an amino acid sequence at least, for example, 95% "identical" to the amino acid sequence of SEQ ID NO:2, for example, it is intended that the amino acid sequence of the polypeptide is identical to the reference sequence except that the polypeptide sequence may include up to five amino acid alterations per each 100 amino acids of the amino acid sequence of SEQ ID NO:2, for example. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is, for instance, 95% identical to the amino acid sequence shown in SEQ ID NO: 2, or to the amino acid sequence encoded by deposited DNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Another aspect of the present invention provides a nucleic acid molecule encoding the polypeptide comprising the amino acid sequence selected from the group consisting of SEQ ID NO:6, SEQ ID NO:8, SEQ ID NO:10, SEQ ID NO:12, SEQ ID NO:14, SEQ ID NO:16 and SEQ ID NO:18. Preferably, the invention provides for nucleic acid molecules, which code for the aforementioned polypeptides, that are selected from the group consisting of SEQ ID NO:5, SEQ ID NO:7, SEQ ID NO:9, SEQ ID NO:11, SEQ ID NO:13, SEQ ID NO:15 and SEQ ID NO:17.

Accordingly, SEQ ID NO:5 corresponds to the nucleic acid sequence that codes for the amino acid sequence of SEQ ID NO:6. SEQ ID NO:7 corresponds to the nucleic acid sequence that codes for the amino acid sequence of SEQ ID NO:8. SEQ ID NO:9 corresponds to the nucleic acid sequence that codes for the amino acid sequence of SEQ ID NO:10. SEQ ID NO:11 corresponds to the nucleic acid sequence that codes for the amino acid sequence of SEQ ID NO:12. SEQ ID NO:13 corresponds to the nucleic acid sequence that codes for the amino acid sequence of SEQ ID NO:14. SEQ ID NO:15 corresponds to the nucleic acid sequence that codes for the amino acid sequence of SEQ ID NO:16. SEQ ID NO:17 corresponds to the nucleic acid sequence that codes for the amino acid sequence of SEQ ID NO:18.

Methods used and described herein are well known in the art and are more particularly described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); P. F. Smith-Keary, *Molecular Genetics of Escherichia coli*, The Guilford Press, New York, N.Y. (1989); *Plasmids: A Practical Approach*, 2nd Edition, Hardy, K. D., ed., Oxford University Press, New York, N.Y. (1993); *Vectors: Essential Data*, Gacesa, P., and Ramji, D. P., eds., John Wiley & Sons Pub., New York, N.Y. (1994); *Guide to Electroporation and electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of Plasmids*, Summers, D. K., Blackwell Science, Cambridge, Mass. (1996); *Understanding DNA and Gene Cloning: A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al, eds., Butterworth, Boston, Mass. (1988); *Bacterial Conjugation*, Clewell, D. B., ed., Plenum Press, New York, N.Y. (1993); Del Solar, G., et al., Replication and control of circular bacterial plasmids," *Microbiol Mol. Biol. Rev.* 62:434-464 (1998); Meijer, W. J., et al., "Rolling-circle plasmids from *Bacillus subtilis*: complete nucleotide sequences and analyses of genes of pTA1015, pTA1040, pTA1050 and pTA1060, and comparisons with related plasmids from gram-positive bacteria," *FEMS Microbiol. Rev.* 21:337-368 (1998); Khan, S. A., "Rolling-circle replication of bacterial plasmids," *Microbiol. Mol. Biol. Rev.* 61:442-455 (1997); Baker, R. L., "Protein expression using ubiquitin fusion and cleavage," *Curr. Opin. Biotechnol.* 7:541-546 (1996); Makrides, S. C., "Strategies for achieving high-level expression of genes in *Escherichia coli*," *Microbiol. Rev.* 60:512-538 (1996); Alonso, J. C., et al., "Site-specific recombination in gram-positive theta-replicating plasmids," *FEMS Microbiol. Lett.* 142:1-10 (1996); Miroux, B., et al., "Over-production of protein in *Escherichia coli*: mutant hosts that allow synthesis of some membrane protein and globular protein at high levels," *J. Mol. Biol.* 260:289-298 (1996); Kurland, C. G., and Dong, H., "Bacterial growth inhibited by overproduction of protein," *Mol. Microbiol.* 21:1-4 (1996); Saki, H., and Komano, T., "DNA replication of IncQ broad-host-range plasmids in gram-negative bacteria," *Biosci. Biotechnol. Biochem.* 60:377-382 (1996); Deb, J. K., and Nath, N., "Plasmids of corynebacteria," *FEMS Microbiol. Lett.* 175:11-20 (1999); Smith, G. P., "Filamentous phages as cloning vectors," *Biotechnol.* 10:61-83 (1988); Espinosa, M., et al, "Plasmid rolling cicle replication and its control," *FEMS Microbiol. Lett.* 130:111-120 (1995); Lanka, E., and Wilkins, B. M., "DNA processing reaction in bacterial conjugation," *Ann. Rev. Biochem.* 64:141-169 (1995); Dreiseikelmann, B., "Translocation of DNA across bacterial membranes," *Microbiol. Rev.* 58:293-316 (1994); Nordstrom, K., and Wagner, E. G., "Kinetic aspects of control of plasmid replication by antisense RNA," *Trends Biochem. Sci.* 19:294-300 (1994); Frost, L. S., et al, "Analysis of the sequence gene products of the transfer region of the F sex factor," *Microbiol. Rev.* 58:162-210 (1994); Drury, L., "Transformation of bacteria by electroporation," *Methods Mol. Biol.* 58:249-256 (1996); Dower, W. J., "Electroporation of bacteria: a general approach to genetic transformation," *Genet. Eng.* 12:275-295 (1990); Na, S., et al., "The factors affecting transformation efficiency of coryneform bacteria by electroporation," *Chin. J. Biotechnol.* 11:193-198 (1995); Pansegrau, W., "Covalent association of the traI gene product of plasmid RP4 with the 5'-terminal nucleotide at the relaxation nick site," *J. Biol. Chem.* 265:10637-10644 (1990); and Bailey, J. E., "Host-vector interactions in *Escherichia coli*," *Adv. Biochem. Eng. Biotechnol.* 48:29-52 (1993).

EXAMPLES

The following examples are illustrative only and are not intended to limit the scope of the invention as defined by the appended claims.

Strains and Media

Bacterial strains used were *Corynebacterium glutamicum* ATCC 21253 and NRRL B-11474. These strains have an auxotrophy for homoserine (ATCC 21253) and for threonine, methionine and alanine (NRRL B-11474).

Defined medium for *Corynebacterium glutamicum* ATCC 21253 contained the following ingredients (per liter): glucose, 20 g; NaCl, 2 g; citrate (trisodium salt, dihydrate), 3 g; $CaCl_2.2H_2O$, 0.1 g; $MgSO_4.7H_2O$, 0.5 g; $Na_2EDTA.2H_2O$, 75 mg; $FeSO_4.7H_2O$, 50 mg; 100× salt solution, 20 ml; $K_2HPO_4$, 4 g; $KH_2PO_4$, 2 g; $(NH_4)_2SO_4$, 7.5 g; urea, 3.75 g; leucine, 0.1 g; threonine, 0.15 g; methionine, 0.05 g; thiamine, 0.45 mg; biotin, 0.45 mg; pantothenic acid, 4.5 mg (pH 7.0). The salt solution contained the following ingredients (per liter): $MnSO_4$, 200 mg; $Na_2B_4O_7.10H_2O$, 20 mg; $(NH_4)_6Mo_7O_{24}.4H_2O$, 10 mg; $FeCl_3.6H_2O$, 200 mg; $ZnSO_4.7H_2O$, 50 mg; $CuCl_2.2H_2O$, 20 mg (pH 2.0).

Defined medium for *Corynebacterium glutamicum* NRRL B-11474 contained the following ingredients (per liter): glucose, 20 g; NaCl, 1 g, $MgSO_4.7H_2O$, 0.4 g; $FeSO_4.7H_2O$, 0.01 g; $MnSO_4.H_2O$, 0.01 g; $KH_2PO_4$, 1 g; $(NH_4)_2SO_4$, 10 g; urea, 2.5 g; alanine, 0.5 g; threonine, 0.25 g; methionine, 0.5 g; thiamine, 0.45 mg; biotin, 0.45 mg; niacinamide, 50 mg (pH 7.2).

Pyruvate Carboxylase and Phosphoenol Pyruvate Carboxylase Assay

Pyruvate carboxylate and phosphoenol pyruvate carboxylate assays were performed with permeabilized cells prepared by the following method. Log phase cells were harvested by centrifugation for 10 min at 5000 xg at 4° C.

and washed with 20 ml of the ice-cold washing buffer (50 mM Tris/HCl [pH 6.3] containing 50 mM NaCl). The cell pellet was resuspended in an ice-cold Hepes buffer (100 mM Hepes [pH 7.5] containing 20% Glycerol) to reach a final concentration of 25 g dry cell weight/liter. Resuspended cells were permeabilized by adding 30 µl of a 10% Hexadecyltrimethyl-ammonium bromide (CTAB) (w/v) solution to 1 ml of cells to give a final concentration of 0.3% (CTAB)(v/v).

For determination of pyruvate carboxylate activity, the assay mixture contained 10 mM pyruvic acid, 14 mM $KHCO_3$, 4 mM $MgCl_2$, 1.75 mM ATP, 50 µmole acetyl-CoA, 0.3 mg bovine serum albumin, 0.055 U citrate synthase and 50 mM sodium phosphate buffer ([pH 7.5] containing 0.1 mg 5,5'-Dithio-bis(2-nitrobenzoic acid) (DTNB)) in a final volume of 1 ml. The reaction was started at 30° C. with the addition of 10 µl of the permeabilized cell suspension, and the formation of DTNB-thiophenolate was followed over time at 412 nm. Relevant standards and controls were carried out in the same manner.

For determination of phosphoenol pyruvate carboxylase activity, the assay mixture contained 10 mM phosphoenol pyruvate, 14 mM $KHCO_3$, 4 mM $MgCl_2$, 50 µmole acetyl-CoA, 0.3 mg bovine serum albumin, 0.055 U citrate synthase and 50 mM sodium phosphate buffer ([pH 7.5] containing 0.1 mg 5,5'-Dithio-bis(2-nitrobenzoic acid) (DTNB)) in a final volume of 1 ml. The reaction was carried out in the same conditions described for the pyruvate carboxylase assay.

The reproducibility for enzyme assays was typically 10%.

DNA Isolation and Purification

DNA was isolated from cultures of NRRL B-11474 cells. Defined media for NRRL B-11474 (CM media) contain the following ingredients, per liter: sucrose, 50 g; $KH_2PO_4$, 0.5 g; $K_2HPO_4$, 1.5 g; urea, 3 g; $MgSO_4.7H_2O$, 0.5 g; polypeptone, 20 g; beef extract, 5 g; biotin, 12.5 ml (60 mg/L); thiamine, 25 ml (120 mg/L), niacinamide, 25 ml (5 g/L); L-methionine, 0.5 g; L-threonine, 0.25 g; L-alanine, 0.5 g. NRRL B-11474 cells were harvested from CM media and suspended in 10 ml of TE, pH 8 (10 mM Tris*Cl, 1 mM EDTA). Forty micrograms of RNase A and 10 milligrams of lysozyme were added per milliliter of suspension and the suspension was incubated at 37° C. for 30 minutes. The suspension was made in 1.0% in sodiumdodecyl sulfate (SDS) and 0.1 mg/l proteinase K was added, and the cells were lysed by incubation at 37° C. for 10 minutes. Nucleic acids were purified by three extractions with TE-saturated phenol (pH7), followed by ethanol precipitation. Nucleic acid precipitates were twice washed with 80% ethanol and redissolved in TE pH 8.

The concentrations of DNA were quantified spectrophotometrically at 260 nm. Purity of DNA preparations were determined spectrophotometrically (A260/A280 and A26JA230 ratios) and by agarose gel electrophoresis (0.8% agarose in 1× TAE).

Sequencing of the genomic DNA was performed, as is known by one of ordinary skill in the art, by creating libraries of plasmids and cosmids using pGEM3 and Lorist 6 respectively. Briefly, a Sau3AI digestion was performed on the genomic DNA and inserted into the BamHI site of pGEM3. The forward primer was used to generate a sequence, and primer walking generated the remainder of the sequence.

Activity of Pyruvate Carboxylase

Development of a Continuous Assay for Determining Pyruvate Carboxylase Activity

A discontinuous assay for determining pyruvate carboxylase from permeabilized cells has been previously described (Peters-Wendisch, P. G. et al. *Microbiology*, 143: 1095-1103 (1997)). Because of the central location of OAA in the metabolism, it seemed to be that OAA would accumulate during the first reaction of the discontinuous assay. Most likely, OAA would be lost to other products, because of the competing enzymes that are still active. This depletion of OAA would inevitably lead to the underestimation of pyruvate carboxylase activity. To verify this assumption of decreasing OAA concentrations, a known amount of OAA was added to the first reaction in presence of permeabilized and non-permeabilized cells. A significant loss of OAA was detected, demonstrating that permeabilized cells are capable of further transformation of OAA.

To account for the intrinsic loss of OAA during the experiment, a continuous assay was carried out by coupling the two-reaction assay to a one-reaction assay in presence of an excess of citrate synthase. The amount of permeabilized cells added in the assay was optimized to obtain a detectable activity, with the lowest possible background absorbency due to the presence of cells.

To confirm that the continuous assay specifically detected pyruvate carboxylase activity, controls were carried out by assaying for activity in absence of each reaction component (Table 1). Using these controls, the detected activity was determined to be a carboxylation reaction requiring pyruvate, Mg and ATP.

TABLE 1

Controls for the continuous pyruvate carboxylate assay.

| Control | Detected Activity (Abs/min.mg DCW) |
|---|---|
| Complete mixture | 0.30 |
| Cells omitted | 0 |
| Pyruvate omitted | 0.01 |
| $KHCO_3$ omitted | 0.03 |
| $MgCl_2$ omitted | 0.02 |
| ATP omitted | 0.03 |
| Citrate synthase omitted | 0.10 |
| Complete + biotin | 0.35 |
| Complete + avidin | Not determined yet |

To optimize the assay, the influence of the ratio of CTAB:cells was tested. Maximal activity was measured between 8 and 24 mg CTAB/mg dry cell weight (DCW). Pyruvate carboxylase activity was measured in cells incubated with CTAB with varying incubation times. The activity of pyruvate carboxylase remained constant within 0 and 5 minutes. Similarly, different concentrations of DTNB, within the range 0.1-0.3 g/l, gave identical pyruvate carboxylase activity. To confirm the ability of the assay for determining pyruvate carboxylase activity in *Corynebacterium glutamicum*, different quantities of cells were used. Linearity between enzyme activity and quantity of cells was observed within the range 0-0.3 mg DCW.

Figure 3B:
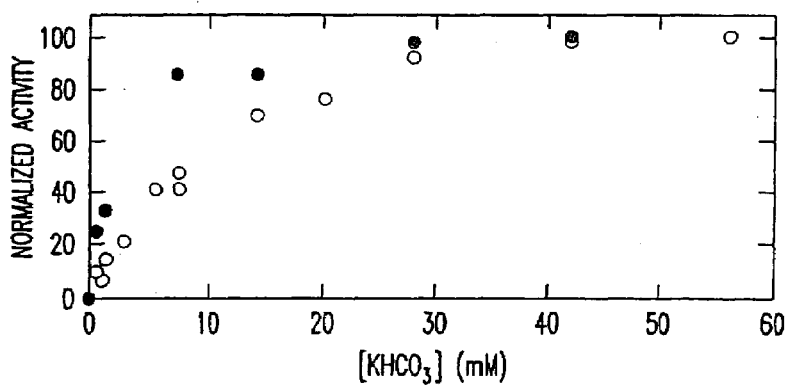
Figure 3C:
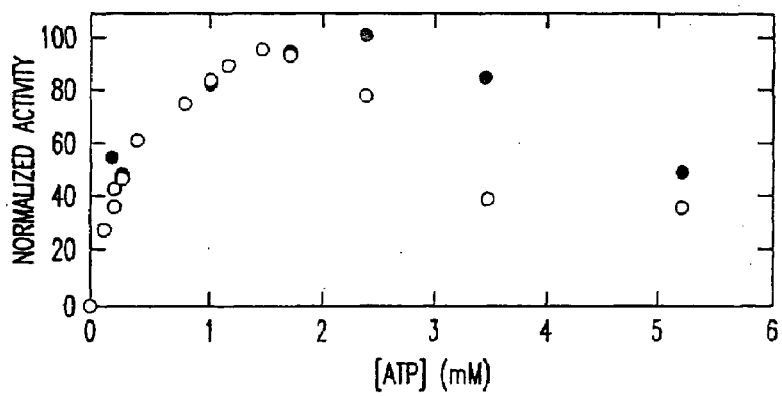
Figure 4:
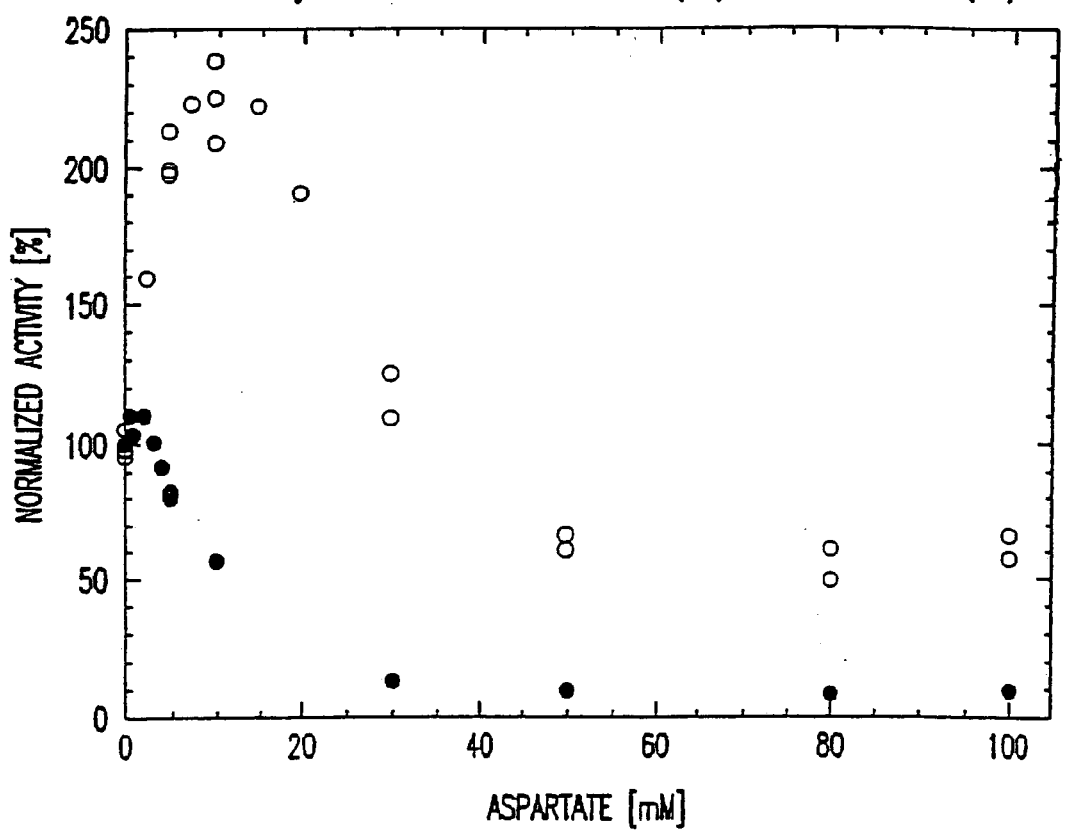
FIG. 4 shows the effects of aspartate concentration on the activity of pyruvate carboxylase in *glutamicum* ATCC@1253 and NRRL B-11474.

Enzymology Study of Pyruvate Carboxylase from *Corynebacterium glutamicum*: Behavior of Pyruvate Carboxylase Towards its Substrates Pyruvate carboxylase activity was determined as a function of various concentrations of its substrates: pyruvate, bicarbonate and ATP (FIG. 3). Based on the data generated, the affinity constants of pyruvate carboxylase for its substrates were determined (Table 2). The pyruvate carboxylase from NRRL B-1474 (also known as BF 100) and ATCC21253 strains demonstrated a similar affinity for pyruvate and ATP. Pyruvate carboxylase activity in both strains were inhibited by ATP above a concentration of 2 mM. However pyruvate carboxylase in ATCC21253 had a higher affinity for bicarbonate than pyruvate carboxylase from NRRL B-11474 (BF 100).

TABLE 2

Comparison of affinity constants for substrates on pyruvate carboxylate from *C. glutamicum*, BF100 and ATCC 21253.

| Strain | $K_{M(Pyruvate)}$[mM] | $K_{M(HCO3-)}$[mM] | $K_{M(ATP)}$[mM] |
|---|---|---|---|
| *C. glutamicum* | | | |
| Pyc | 1.3 ± 03 | 14.4 ± | 0.4 ± 0.1 |
| Pyc ATCC 21253 | 0.3 ± 0.1 | 2.9 ± 0.8 | 0.3 ± 0.1 |

Aspartate Inhibition of Pyruvate Carboxylase

Figure 5:
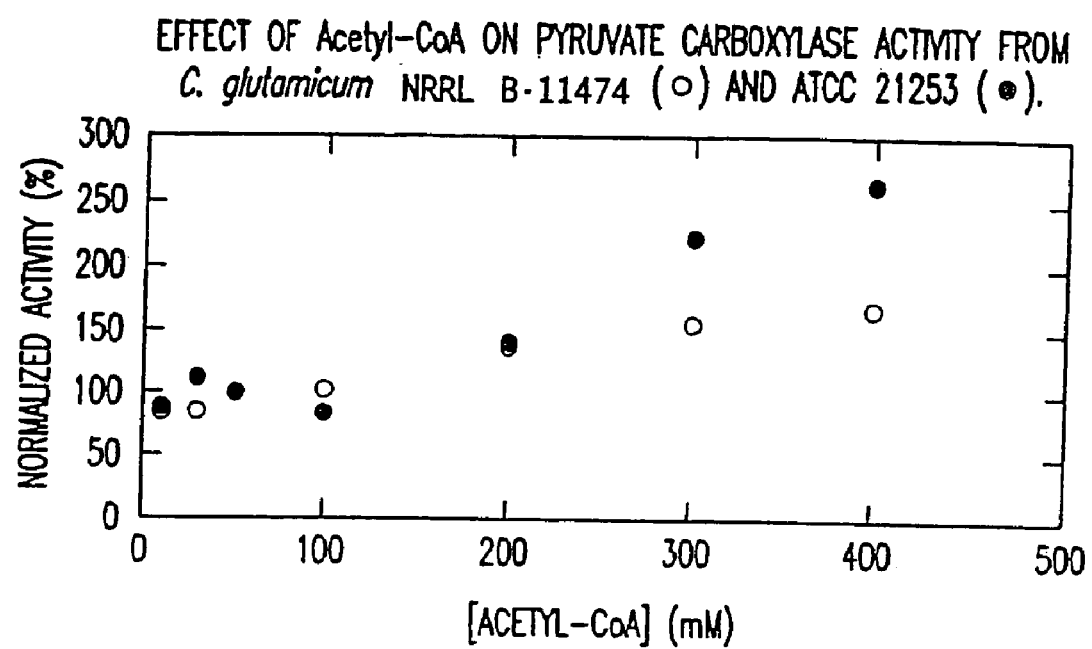
FIG. 5 shows the effects of acetyl-CoA concentration on the activity of pyruvate carboxylase in *C. glutamicum* ATCC-21253 and NRRL B-11474.

Aspartate inhibits phosphoenol pyruvate carboxylase (PEPC) activity. To determine the effect of aspartate on the activity of pyruvate carboxylase, aspartate was added at different concentrations in the spectrophotometer cuvette and enzyme activities were measured. As a comparison, the same experiment was carried out with PEPC in ATCC 21253 (FIG. 5).

The PEPC of *Corynebacterium glutamicum* (ATCC 21253) was found to be strongly inhibited by aspartate. The enzyme was completely inhibited with a concentration of 5 mM aspartate. However, pyruvate carboxylase from the same strain was less sensitive to aspartate, i.e. it retained 35% of its original activity in the presence of 25 mM aspartate.

The pyruvate carboxylase activity in NRRL B-11474 showed a higher basal pyruvate carboxylase activity than ATCC 21253, i.e. the pyruvate carboxylase activity was about 5-times higher in NRRL B-11474 than in the ATCC 21253. Moreover, a dramatic difference in their aspartate inhibition patterns was found. Pyruvate carboxylase from NRRL B-11474 strain was activated by low aspartate concentrations within the range 0-30 mM and inhibited within the range 30-100 mM aspartate. Nevertheless it retained 50% of its original activity, even in the presence of 100 mM aspartate. Activity was maintained at 30% in the presence of 500 mM aspartate. On the other hand, Pyruvate carboxylase from ATCC 21253 was found to be more sensitive to aspartate than pyruvate carboxylase from NRRL B-11474. The pyruvate carboxylase from ATCC21253 lost 70% of its original activity at a concentration of 30 mM aspartate.

The feedback resistant pyruvate carboxylase gene of the present invention was isolated and cloned from NRRL B-11474. The isolated/closed pyruvate carboxylase gene has been deposited in an *E. coli* host cell under deposit NRRL B-30293. Deposit Number NRRL B-30293 was deposited on May 12, 2000 at the Agricultural Research Culture Collection (NRRL) International Depository Authority; 1815 North University Street, Peoria, Ill., 61064 U.S.A. All strains were deposited under the terms of the Budapest Treaty.

Activation of Pyruvate Carboxylase by Acetyl-CoA

Pyruvate carboxylase activity was measured in the presence of different concentrations of acetyl-CoA (FIG. 6). Pyruvate carboxylase activity in both strains increased with increasing acetyl-CoA concentrations. The effect of acetyl-CoA on citrate synthase itself was studied also. Acetyl-CoA had a Km of 10 μM, demonstrating that under our conditions, citrate synthase is saturated with acetyl-CoA. Therefore, the increasing activity of pyruvate carboxylase with increasing acetyl-CoA concentration is the result of acetyl-CoA activating pyruvate carboxylase.

All publications mentioned herein above are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

SEQUENCE LISTING

<160> NUMBER OF SEQ ID NOS: 19

<210> SEQ ID NO 1
<211> LENGTH: 3474
<212> TYPE: DNA
<213> ORGANISM: Corynebacterium glutamicum
<220> FEATURE:
<221> NAME/KEY: CDS
<222> LOCATION: (1)..(3474)

<400> SEQUENCE: 1

```
gtg act gct atc acc ctt ggc ggt ctc ttg ttg aaa gga ata att act        48
Met Thr Ala Ile Thr Leu Gly Gly Leu Leu Leu Lys Gly Ile Ile Thr
1               5                   10                  15 cta gtg tcg act cac aca tct tca acg ctt cca gca ttc aaa aag atc        96
Leu Val Ser Thr His Thr Ser Ser Thr Leu Pro Ala Phe Lys Lys Ile
                20                  25                  30 ttg gta gca aac cgc ggc gaa atc gcg gtc cgt gct ttc cgt gca gca       144
Leu Val Ala Asn Arg Gly Glu Ile Ala Val Arg Ala Phe Arg Ala Ala
            35                  40                  45
```

-continued

```
ctc gaa acc ggt gca gcc acg gta gct att tac ccc cgt gaa gat cgg      192
Leu Glu Thr Gly Ala Ala Thr Val Ala Ile Tyr Pro Arg Glu Asp Arg
 50                  55                  60 gga tca ttc cac cgc tct ttt gct tct gaa gct gtc cgc att ggt act      240
Gly Ser Phe His Arg Ser Phe Ala Ser Glu Ala Val Arg Ile Gly Thr
 65                  70                  75                  80 gaa ggc tca cca gtc aag gcg tac ctg gac atc gat gaa att atc ggt      288
Glu Gly Ser Pro Val Lys Ala Tyr Leu Asp Ile Asp Glu Ile Ile Gly
                     85                  90                  95 gca gct aaa aaa gtt aaa gca gat gct att tac ccg gga tat ggc ttc      336
Ala Ala Lys Lys Val Lys Ala Asp Ala Ile Tyr Pro Gly Tyr Gly Phe
                100                 105                 110 ctg tct gaa aat gcc cag ctt gcc cgc gag tgc gcg gaa aac ggc att      384
Leu Ser Glu Asn Ala Gln Leu Ala Arg Glu Cys Ala Glu Asn Gly Ile
            115                 120                 125 act ttt att ggc cca acc cca gag gtt ctt gat ctc acc ggt gat aag      432
Thr Phe Ile Gly Pro Thr Pro Glu Val Leu Asp Leu Thr Gly Asp Lys
        130                 135                 140 tct cgt gcg gta acc gcc gcg aag aag gct ggt ctg cca gtt ttg gcg      480
Ser Arg Ala Val Thr Ala Ala Lys Lys Ala Gly Leu Pro Val Leu Ala
145                 150                 155                 160 gaa tcc acc ccg agc aaa aac atc gat gac atc gtt aaa agc gct gaa      528
Glu Ser Thr Pro Ser Lys Asn Ile Asp Asp Ile Val Lys Ser Ala Glu
                165                 170                 175 ggc cag act tac ccc atc ttt gta aag gca gtt gcc ggt ggt ggc gga      576
Gly Gln Thr Tyr Pro Ile Phe Val Lys Ala Val Ala Gly Gly Gly Gly
                180                 185                 190 cgc ggt atg cgc ttt gtt tct tca cct gat gag ctc cgc aaa ttg gca      624
Arg Gly Met Arg Phe Val Ser Ser Pro Asp Glu Leu Arg Lys Leu Ala
            195                 200                 205 aca gaa gca tct cgt gaa gct gaa gcg gca ttc ggc gac ggt tcg gta      672
Thr Glu Ala Ser Arg Glu Ala Glu Ala Ala Phe Gly Asp Gly Ser Val
        210                 215                 220 tat gtc gaa cgt gct gtg att aac ccc cag cac att gaa gtg cag atc      720
Tyr Val Glu Arg Ala Val Ile Asn Pro Gln His Ile Glu Val Gln Ile
225                 230                 235                 240 ctt ggc gat cgc act gga gaa gtt gta cac ctt tat gaa cgt gac tgc      768
Leu Gly Asp Arg Thr Gly Glu Val Val His Leu Tyr Glu Arg Asp Cys
                245                 250                 255 tca ctg cag cgt cgt cac caa aaa gtt gtc gaa att gcg cca gca cag      816
Ser Leu Gln Arg Arg His Gln Lys Val Val Glu Ile Ala Pro Ala Gln
                260                 265                 270 cat ttg gat cca gaa ctg cgt gat cgc att tgt gcg gat gca gta aag      864
His Leu Asp Pro Glu Leu Arg Asp Arg Ile Cys Ala Asp Ala Val Lys
            275                 280                 285 ttc tgc cgc tcc att ggt tac cag ggc gcg gga acc gtg gaa ttc ttg      912
Phe Cys Arg Ser Ile Gly Tyr Gln Gly Ala Gly Thr Val Glu Phe Leu
        290                 295                 300 gtc gat gaa aag ggc aac cac gtt ttc atc gaa atg aac cca cgt atc      960
Val Asp Glu Lys Gly Asn His Val Phe Ile Glu Met Asn Pro Arg Ile
305                 310                 315                 320 cag gtt gag cac acc gtg act gaa gaa gtc acc gag gtg gac ctg gtg     1008
Gln Val Glu His Thr Val Thr Glu Glu Val Thr Glu Val Asp Leu Val
                325                 330                 335 aag gcg cag atg cgc ttg gct gct ggt gca acc ttg aag gaa ttg ggt     1056
Lys Ala Gln Met Arg Leu Ala Ala Gly Ala Thr Leu Lys Glu Leu Gly
                340                 345                 350 ctg acc caa gat aag atc aag acc cac ggt gca gca ctg cag tgc cgc     1104
Leu Thr Gln Asp Lys Ile Lys Thr His Gly Ala Ala Leu Gln Cys Arg
```

```
                355                 360                 365
atc acc acg gaa gat cca aac aac ggc ttc cgc cca gat acc gga act      1152
Ile Thr Thr Glu Asp Pro Asn Asn Gly Phe Arg Pro Asp Thr Gly Thr
370                 375                 380 atc acc gcg tac cgc tca cca ggc gga gct ggc gtt cgt ctt gac ggt      1200
Ile Thr Ala Tyr Arg Ser Pro Gly Gly Ala Gly Val Arg Leu Asp Gly
385                 390                 395                 400 gca gct cag ctc ggt ggc gaa atc acc gca cac ttt gac tcc atg ctg      1248
Ala Ala Gln Leu Gly Gly Glu Ile Thr Ala His Phe Asp Ser Met Leu
                405                 410                 415 gtg aaa atg acc tgc cgt ggt tcc gac ttt gaa act gct gtt gct cgt      1296
Val Lys Met Thr Cys Arg Gly Ser Asp Phe Glu Thr Ala Val Ala Arg
        420                 425                 430 gca cag cgc gcg ttg gct gag ttc acc gtg tct ggt gtt gca acc aac      1344
Ala Gln Arg Ala Leu Ala Glu Phe Thr Val Ser Gly Val Ala Thr Asn
        435                 440                 445 att ggt ttc ttg cgt gcg ttg ctg cgg gaa gag gac ttc act tcc aag      1392
Ile Gly Phe Leu Arg Ala Leu Leu Arg Glu Glu Asp Phe Thr Ser Lys
450                 455                 460 cgc atc gcc acc gga ttt atc ggc gat cac cca cac ctc ctt cag gct      1440
Arg Ile Ala Thr Gly Phe Ile Gly Asp His Pro His Leu Leu Gln Ala
465                 470                 475                 480 cca cct gcg gat gat gag cag gga cgc atc ctg gat tac ttg gca gat      1488
Pro Pro Ala Asp Asp Glu Gln Gly Arg Ile Leu Asp Tyr Leu Ala Asp
                485                 490                 495 gtc acc gtg aac aag cct cat ggt gtg cgt cca aag gat gtt gca gca      1536
Val Thr Val Asn Lys Pro His Gly Val Arg Pro Lys Asp Val Ala Ala
            500                 505                 510 cca atc gat aag ctg ccc aac atc aag gat ctg cca ctg cca cgc ggt      1584
Pro Ile Asp Lys Leu Pro Asn Ile Lys Asp Leu Pro Leu Pro Arg Gly
        515                 520                 525 tcc cgt gac cgc ctg aag cag ctt ggc cca gcc gcg ttt gct cgt gat      1632
Ser Arg Asp Arg Leu Lys Gln Leu Gly Pro Ala Ala Phe Ala Arg Asp
530                 535                 540 ctc cgt gag cag gac gca ctg gca gtt act gat acc acc ttc cgc gat      1680
Leu Arg Glu Gln Asp Ala Leu Ala Val Thr Asp Thr Thr Phe Arg Asp
545                 550                 555                 560 gca cac cag tct ttg ctt gcg acc cga gtc cgc tca ttc gca ctg aag      1728
Ala His Gln Ser Leu Leu Ala Thr Arg Val Arg Ser Phe Ala Leu Lys
                565                 570                 575 cct gcg gca gag gcc gtc gca aag ctg act cct gag ctt ttg tcc gtg      1776
Pro Ala Ala Glu Ala Val Ala Lys Leu Thr Pro Glu Leu Leu Ser Val
            580                 585                 590 gag gcc tgg ggc ggc gcg acc tac gat gtg gcg atg cgt ttc ctc ttt      1824
Glu Ala Trp Gly Gly Ala Thr Tyr Asp Val Ala Met Arg Phe Leu Phe
        595                 600                 605 gag gat ccg tgg gac agg ctc gac gag ctg cgc gag gcg atg ccg aat      1872
Glu Asp Pro Trp Asp Arg Leu Asp Glu Leu Arg Glu Ala Met Pro Asn
610                 615                 620 gta aac att cag atg ctg ctt cgc ggc cgc aac acc gtg gga tac acc      1920
Val Asn Ile Gln Met Leu Leu Arg Gly Arg Asn Thr Val Gly Tyr Thr
625                 630                 635                 640 ccg tac cca gac tcc gtc tgc cgc gcg ttt gtt aag gaa gct gcc agc      1968
Pro Tyr Pro Asp Ser Val Cys Arg Ala Phe Val Lys Glu Ala Ala Ser
                645                 650                 655 tcc ggc gtg gac atc ttc cgc atc ttc gac gcg ctt aac gac gtc tcc      2016
Ser Gly Val Asp Ile Phe Arg Ile Phe Asp Ala Leu Asn Asp Val Ser
            660                 665                 670 cag atg cgt cca gca atc gac gca gtc ctg gag acc aac acc gcg gta      2064
```

-continued

```
                Gln Met Arg Pro Ala Ile Asp Ala Val Leu Glu Thr Asn Thr Ala Val
                        675                 680                 685 gcc gag gtg gct atg gct tat tct ggt gat ctc tct gat cca aat gaa        2112
Ala Glu Val Ala Met Ala Tyr Ser Gly Asp Leu Ser Asp Pro Asn Glu
        690                 695                 700 aag ctc tac acc ctg gat tac tac cta aag atg gca gag gag atc gtc        2160
Lys Leu Tyr Thr Leu Asp Tyr Tyr Leu Lys Met Ala Glu Glu Ile Val
705                 710                 715                 720 aag tct ggc gct cac att ctg gcc att aag gat atg gct ggt ctg ctt        2208
Lys Ser Gly Ala His Ile Leu Ala Ile Lys Asp Met Ala Gly Leu Leu
                725                 730                 735 cgc cca gct gcg gta acc aag ctg gtc acc gca ctg cgc cgt gaa ttc        2256
Arg Pro Ala Ala Val Thr Lys Leu Val Thr Ala Leu Arg Arg Glu Phe
            740                 745                 750 gat ctg cca gtg cac gtg cac acc cac gac act gcg ggt ggc cag ttg        2304
Asp Leu Pro Val His Val His Thr His Asp Thr Ala Gly Gly Gln Leu
        755                 760                 765 gct acc tac ttt gct gca gct caa gct ggt gca gat gct gtt gac ggt        2352
Ala Thr Tyr Phe Ala Ala Ala Gln Ala Gly Ala Asp Ala Val Asp Gly
    770                 775                 780 gct tcc gca cca ctg tct ggc acc acc tcc cag cca tcc ctg tct gcc        2400
Ala Ser Ala Pro Leu Ser Gly Thr Thr Ser Gln Pro Ser Leu Ser Ala
785                 790                 795                 800 att gtt gct gca ttc gcg cac acc cgt cgc gat acc ggt ttg agc ctc        2448
Ile Val Ala Ala Phe Ala His Thr Arg Arg Asp Thr Gly Leu Ser Leu
                805                 810                 815 gag gct gtt tct gac ctc gag ccg tac tgg gaa gct gtg cgc gga ctg        2496
Glu Ala Val Ser Asp Leu Glu Pro Tyr Trp Glu Ala Val Arg Gly Leu
            820                 825                 830 tac ctg cca ttt gag tct gga acc cca ggc cca acc ggt cgc gtc tac        2544
Tyr Leu Pro Phe Glu Ser Gly Thr Pro Gly Pro Thr Gly Arg Val Tyr
        835                 840                 845 cgc cac gaa atc cca ggc gga cag ttg tcc aac ctg cgt gca cag gcc        2592
Arg His Glu Ile Pro Gly Gly Gln Leu Ser Asn Leu Arg Ala Gln Ala
    850                 855                 860 acc gca ctg ggc ctt gct gat cgc ttc gag ctc atc gaa gac aac tac        2640
Thr Ala Leu Gly Leu Ala Asp Arg Phe Glu Leu Ile Glu Asp Asn Tyr
865                 870                 875                 880 gca gcc gtt aat gag atg ctg gga cgc cca acc aag gtc acc cca tcc        2688
Ala Ala Val Asn Glu Met Leu Gly Arg Pro Thr Lys Val Thr Pro Ser
                885                 890                 895 tcc aag gtt gtt ggc gac ctc gca ctc cac ctg gtt ggt gcg ggt gta        2736
Ser Lys Val Val Gly Asp Leu Ala Leu His Leu Val Gly Ala Gly Val
            900                 905                 910 gat cca gca gac ttt gct gca gac cca caa aag tac gac atc cca gac        2784
Asp Pro Ala Asp Phe Ala Ala Asp Pro Gln Lys Tyr Asp Ile Pro Asp
        915                 920                 925 tct gtc atc gcg ttc ctg cgc ggc gag ctt ggt aac cct cca ggt ggc        2832
Ser Val Ile Ala Phe Leu Arg Gly Glu Leu Gly Asn Pro Pro Gly Gly
    930                 935                 940 tgg cca gaa cca ctg cgc acc cgc gca ctg gaa ggc cgc tcc gaa ggc        2880
Trp Pro Glu Pro Leu Arg Thr Arg Ala Leu Glu Gly Arg Ser Glu Gly
945                 950                 955                 960 aag gca cct ctg acg gaa gtt cct gag gaa gag cag gcg cac ctc gac        2928
Lys Ala Pro Leu Thr Glu Val Pro Glu Glu Glu Gln Ala His Leu Asp
                965                 970                 975 gct gat gat tcc aag gaa cgt cgc aac agc ctc aac cgc ctg ctg ttc        2976
Ala Asp Asp Ser Lys Glu Arg Arg Asn Ser Leu Asn Arg Leu Leu Phe
            980                 985                 990
```

```
ccg aag cca acc gaa gag ttc ctc gag cac cgt cgc cgc ttc ggc aac    3024
Pro Lys Pro Thr Glu Glu Phe Leu Glu His Arg Arg Arg Phe Gly Asn
        995                 1000                1005 acc tct gcg ctg gat gat cgt gaa ttc ttc tac gga ctg gtc gag        3069
Thr Ser Ala Leu Asp Asp Arg Glu Phe Phe Tyr Gly Leu Val Glu
    1010                1015                1020 ggc cgc gag act ttg atc cgc ctg cca gat gtg cgc acc cca ctg        3114
Gly Arg Glu Thr Leu Ile Arg Leu Pro Asp Val Arg Thr Pro Leu
    1025                1030                1035 ctt gtt cgc ctg gat gcg atc tct gag cca gac gat aag ggt atg        3159
Leu Val Arg Leu Asp Ala Ile Ser Glu Pro Asp Asp Lys Gly Met
    1040                1045                1050 cgc aat gtt gtg gcc aac gtc aac ggc cag atc cgc cca atg cgt        3204
Arg Asn Val Val Ala Asn Val Asn Gly Gln Ile Arg Pro Met Arg
    1055                1060                1065 gtg cgt gac cgc tcc gtt gag tct gtc acc gca acc gca gaa aag        3249
Val Arg Asp Arg Ser Val Glu Ser Val Thr Ala Thr Ala Glu Lys
    1070                1075                1080 gca gat tcc tcc aac aag ggc cat gtt gct gca cca ttc gct ggt        3294
Ala Asp Ser Ser Asn Lys Gly His Val Ala Ala Pro Phe Ala Gly
    1085                1090                1095 gtt gtc act gtg act gtt gct gaa ggt gat gag gtc aag gct gga        3339
Val Val Thr Val Thr Val Ala Glu Gly Asp Glu Val Lys Ala Gly
    1100                1105                1110 gat gca gtc gca atc atc gag gct atg aag atg gaa gca aca atc        3384
Asp Ala Val Ala Ile Ile Glu Ala Met Lys Met Glu Ala Thr Ile
    1115                1120                1125 act gct tct gtt gac ggc aag att gaa cgc gtt gtg gtt cct gct        3429
Thr Ala Ser Val Asp Gly Lys Ile Glu Arg Val Val Val Pro Ala
    1130                1135                1140 gca acg aag gtg gaa ggt ggc gac ttg atc gtc gtc gtt tcc taa        3474
Ala Thr Lys Val Glu Gly Gly Asp Leu Ile Val Val Val Ser
    1145                1150                1155

<210> SEQ ID NO 2
<211> LENGTH: 1157
<212> TYPE: PRT
<213> ORGANISM: Corynebacterium glutamicum

<400> SEQUENCE: 2

Met Thr Ala Ile Thr Leu Gly Gly Leu Leu Leu Lys Gly Ile Ile Thr
1               5                   10                  15

Leu Val Ser Thr His Thr Ser Ser Thr Leu Pro Ala Phe Lys Lys Ile
            20                  25                  30

Leu Val Ala Asn Arg Gly Glu Ile Ala Val Arg Ala Phe Arg Ala Ala
        35                  40                  45

Leu Glu Thr Gly Ala Ala Thr Val Ala Ile Tyr Pro Arg Glu Asp Arg
    50                  55                  60

Gly Ser Phe His Arg Ser Phe Ala Ser Glu Ala Val Arg Ile Gly Thr
65                  70                  75                  80

Glu Gly Ser Pro Val Lys Ala Tyr Leu Asp Ile Asp Glu Ile Ile Gly
                85                  90                  95

Ala Ala Lys Lys Val Lys Ala Asp Ala Ile Tyr Pro Gly Tyr Gly Phe
            100                 105                 110

Leu Ser Glu Asn Ala Gln Leu Ala Arg Glu Cys Ala Glu Asn Gly Ile
        115                 120                 125

Thr Phe Ile Gly Pro Thr Pro Glu Val Leu Asp Leu Thr Gly Asp Lys
    130                 135                 140
```

-continued

```
Ser Arg Ala Val Thr Ala Ala Lys Lys Ala Gly Leu Pro Val Leu Ala
145                 150                 155                 160

Glu Ser Thr Pro Ser Lys Asn Ile Asp Asp Ile Val Lys Ser Ala Glu
                165                 170                 175

Gly Gln Thr Tyr Pro Ile Phe Val Lys Ala Val Ala Gly Gly Gly Gly
            180                 185                 190

Arg Gly Met Arg Phe Val Ser Ser Pro Asp Glu Leu Arg Lys Leu Ala
        195                 200                 205

Thr Glu Ala Ser Arg Glu Ala Glu Ala Phe Gly Asp Gly Ser Val
    210                 215                 220

Tyr Val Glu Arg Ala Val Ile Asn Pro Gln His Ile Glu Val Gln Ile
225                 230                 235                 240

Leu Gly Asp Arg Thr Gly Glu Val Val His Leu Tyr Glu Arg Asp Cys
                245                 250                 255

Ser Leu Gln Arg Arg His Gln Lys Val Val Glu Ile Ala Pro Ala Gln
                260                 265                 270

His Leu Asp Pro Glu Leu Arg Asp Arg Ile Cys Ala Asp Ala Val Lys
            275                 280                 285

Phe Cys Arg Ser Ile Gly Tyr Gln Gly Ala Gly Thr Val Glu Phe Leu
        290                 295                 300

Val Asp Glu Lys Gly Asn His Val Phe Ile Glu Met Asn Pro Arg Ile
305                 310                 315                 320

Gln Val Glu His Thr Val Thr Glu Glu Val Thr Glu Val Asp Leu Val
                325                 330                 335

Lys Ala Gln Met Arg Leu Ala Ala Gly Ala Thr Leu Lys Glu Leu Gly
                340                 345                 350

Leu Thr Gln Asp Lys Ile Lys Thr His Gly Ala Ala Leu Gln Cys Arg
            355                 360                 365

Ile Thr Thr Glu Asp Pro Asn Asn Gly Phe Arg Pro Asp Thr Gly Thr
        370                 375                 380

Ile Thr Ala Tyr Arg Ser Pro Gly Gly Ala Gly Val Arg Leu Asp Gly
385                 390                 395                 400

Ala Ala Gln Leu Gly Gly Glu Ile Thr Ala His Phe Asp Ser Met Leu
                405                 410                 415

Val Lys Met Thr Cys Arg Gly Ser Asp Phe Glu Thr Ala Val Ala Arg
                420                 425                 430

Ala Gln Arg Ala Leu Ala Glu Phe Thr Val Ser Gly Val Ala Thr Asn
            435                 440                 445

Ile Gly Phe Leu Arg Ala Leu Leu Arg Glu Glu Asp Phe Thr Ser Lys
        450                 455                 460

Arg Ile Ala Thr Gly Phe Ile Gly Asp His Pro His Leu Leu Gln Ala
465                 470                 475                 480

Pro Pro Ala Asp Asp Glu Gln Gly Arg Ile Leu Asp Tyr Leu Ala Asp
                485                 490                 495

Val Thr Val Asn Lys Pro His Gly Val Arg Pro Lys Asp Val Ala Ala
            500                 505                 510

Pro Ile Asp Lys Leu Pro Asn Ile Lys Asp Leu Pro Leu Pro Arg Gly
        515                 520                 525

Ser Arg Asp Arg Leu Lys Gln Leu Gly Pro Ala Ala Phe Ala Arg Asp
    530                 535                 540

Leu Arg Glu Gln Asp Ala Leu Ala Val Thr Asp Thr Thr Phe Arg Asp
545                 550                 555                 560

Ala His Gln Ser Leu Leu Ala Thr Arg Val Arg Ser Phe Ala Leu Lys
```

-continued

```
                565                 570                 575
Pro Ala Ala Glu Ala Val Ala Lys Leu Thr Pro Glu Leu Leu Ser Val
                580                 585                 590
Glu Ala Trp Gly Gly Ala Thr Tyr Asp Val Ala Met Arg Phe Leu Phe
                595                 600                 605
Glu Asp Pro Trp Asp Arg Leu Asp Glu Leu Arg Glu Ala Met Pro Asn
            610                 615                 620
Val Asn Ile Gln Met Leu Leu Arg Gly Arg Asn Thr Val Gly Tyr Thr
625                 630                 635                 640
Pro Tyr Pro Asp Ser Val Cys Arg Ala Phe Val Lys Glu Ala Ala Ser
                645                 650                 655
Ser Gly Val Asp Ile Phe Arg Ile Phe Asp Ala Leu Asn Asp Val Ser
                660                 665                 670
Gln Met Arg Pro Ala Ile Asp Ala Val Leu Glu Thr Asn Thr Ala Val
            675                 680                 685
Ala Glu Val Ala Met Ala Tyr Ser Gly Asp Leu Ser Asp Pro Asn Glu
            690                 695                 700
Lys Leu Tyr Thr Leu Asp Tyr Tyr Leu Lys Met Ala Glu Glu Ile Val
705                 710                 715                 720
Lys Ser Gly Ala His Ile Leu Ala Ile Lys Asp Met Ala Gly Leu Leu
                725                 730                 735
Arg Pro Ala Ala Val Thr Lys Leu Val Thr Ala Leu Arg Arg Glu Phe
                740                 745                 750
Asp Leu Pro Val His Val His Thr His Asp Thr Ala Gly Gly Gln Leu
            755                 760                 765
Ala Thr Tyr Phe Ala Ala Gln Ala Gly Ala Asp Ala Val Asp Gly
            770                 775                 780
Ala Ser Ala Pro Leu Ser Gly Thr Thr Ser Gln Pro Ser Leu Ser Ala
785                 790                 795                 800
Ile Val Ala Ala Phe Ala His Thr Arg Arg Asp Thr Gly Leu Ser Leu
                805                 810                 815
Glu Ala Val Ser Asp Leu Glu Pro Tyr Trp Glu Ala Val Arg Gly Leu
            820                 825                 830
Tyr Leu Pro Phe Glu Ser Gly Thr Pro Gly Pro Thr Gly Arg Val Tyr
            835                 840                 845
Arg His Glu Ile Pro Gly Gly Gln Leu Ser Asn Leu Arg Ala Gln Ala
            850                 855                 860
Thr Ala Leu Gly Leu Ala Asp Arg Phe Glu Leu Ile Glu Asp Asn Tyr
865                 870                 875                 880
Ala Ala Val Asn Glu Met Leu Gly Arg Pro Thr Lys Val Thr Pro Ser
                885                 890                 895
Ser Lys Val Val Gly Asp Leu Ala Leu His Leu Val Gly Ala Gly Val
                900                 905                 910
Asp Pro Ala Asp Phe Ala Ala Asp Pro Gln Lys Tyr Asp Ile Pro Asp
            915                 920                 925
Ser Val Ile Ala Phe Leu Arg Gly Glu Leu Gly Asn Pro Pro Gly Gly
            930                 935                 940
Trp Pro Glu Pro Leu Arg Thr Arg Ala Leu Glu Gly Arg Ser Glu Gly
945                 950                 955                 960
Lys Ala Pro Leu Thr Glu Val Pro Glu Glu Gln Ala His Leu Asp
                965                 970                 975
Ala Asp Asp Ser Lys Glu Arg Arg Asn Ser Leu Asn Arg Leu Leu Phe
            980                 985                 990
```

Pro Lys Pro Thr Glu Glu Phe Leu  Glu His Arg Arg  Phe Gly Asn
        995                 1000                1005

Thr Ser  Ala Leu Asp Asp Arg  Glu Phe Phe Tyr  Gly  Leu Val Glu
    1010             1015                1020

Gly Arg  Glu Thr Leu Ile Arg  Leu Pro Asp Val  Arg  Thr Pro Leu
    1025             1030                1035

Leu Val  Arg Leu Asp Ala Ile  Ser Glu Pro Asp  Asp  Lys Gly Met
    1040             1045                1050

Arg Asn  Val Val Ala Asn Val  Asn Gly Gln Ile  Arg  Pro Met Arg
    1055             1060                1065

Val Arg  Asp Arg Ser Val Glu  Ser Val Thr Ala  Thr  Ala Glu Lys
    1070             1075                1080

Ala Asp  Ser Ser Asn Lys Gly  His Val Ala Ala  Pro  Phe Ala Gly
    1085             1090                1095

Val Val  Thr Val Thr Val Ala  Glu Gly Asp Glu  Val  Lys Ala Gly
    1100             1105                1110

Asp Ala  Val Ala Ile Ile Glu  Ala Met Lys Met  Glu  Ala Thr Ile
    1115             1120                1125

Thr Ala  Ser Val Asp Gly Lys  Ile Glu Arg Val  Val  Val Pro Ala
    1130             1135                1140

Ala Thr  Lys Val Glu Gly Gly  Asp Leu Ile Val  Val  Val Ser
    1145             1150                1155

<210> SEQ ID NO 3

<400> SEQUENCE: 3

000

<210> SEQ ID NO 4

<400> SEQUENCE: 4

000

<210> SEQ ID NO 5
<211> LENGTH: 39
<212> TYPE: DNA
<213> ORGANISM: Corynebacterium glutamicum

<400> SEQUENCE: 5
ccgagcaaaa acatcgatga catcgttaaa agcgctgaa                           39

<210> SEQ ID NO 6
<211> LENGTH: 13
<212> TYPE: PRT
<213> ORGANISM: Corynebacterium glutamicum

<400> SEQUENCE: 6

Pro Ser Lys Asn Ile Asp Asp Ile Val Lys Ser Ala Glu
1               5                   10

<210> SEQ ID NO 7
<211> LENGTH: 39
<212> TYPE: DNA
<213> ORGANISM: Corynebacterium glutamicum

<400> SEQUENCE: 7
cgcggtatgc gctttgtttc ttcacctgat gagctccgc                           39

```
<210> SEQ ID NO 8
<211> LENGTH: 13
<212> TYPE: PRT
<213> ORGANISM: Corynebacterium glutamicum

<400> SEQUENCE: 8

Arg Gly Met Arg Phe Val Ser Ser Pro Asp Glu Leu Arg
1               5                   10

<210> SEQ ID NO 9
<211> LENGTH: 39
<212> TYPE: DNA
<213> ORGANISM: Corynebacterium glutamicum

<400> SEQUENCE: 9
gcggcattcg gcgacggttc ggtatatgtc gaacgtgct                              39

<210> SEQ ID NO 10
<211> LENGTH: 13
<212> TYPE: PRT
<213> ORGANISM: Corynebacterium glutamicum

<400> SEQUENCE: 10

Ala Ala Phe Gly Asp Gly Ser Val Tyr Val Glu Arg Ala
1               5                   10

<210> SEQ ID NO 11
<211> LENGTH: 39
<212> TYPE: DNA
<213> ORGANISM: Corynebacterium glutamicum

<400> SEQUENCE: 11
gtgcagatcc ttggcgatcg cactggagaa gttgtacac                              39

<210> SEQ ID NO 12
<211> LENGTH: 13
<212> TYPE: PRT
<213> ORGANISM: Corynebacterium glutamicum

<400> SEQUENCE: 12

Val Gln Ile Leu Gly Asp Arg Thr Gly Glu Val Val His
1               5                   10

<210> SEQ ID NO 13
<211> LENGTH: 39
<212> TYPE: DNA
<213> ORGANISM: Corynebacterium glutamicum

<400> SEQUENCE: 13
atcgccaccg gatttatcgg cgatcaccca cacctcctt                              39

<210> SEQ ID NO 14
<211> LENGTH: 13
<212> TYPE: PRT
<213> ORGANISM: Corynebacterium glutamicum

<400> SEQUENCE: 14

Ile Ala Thr Gly Phe Ile Gly Asp His Pro His Leu Leu
1               5                   10

<210> SEQ ID NO 15
<211> LENGTH: 39
<212> TYPE: DNA
<213> ORGANISM: Corynebacterium glutamicum
```

-continued

<400> SEQUENCE: 15
acaatcactg cttctgttga cggcaagatt gaacgcgtt                                    39

<210> SEQ ID NO 16
<211> LENGTH: 13
<212> TYPE: PRT
<213> ORGANISM: Corynebacterium glutamicum

<400> SEQUENCE: 16

Thr Ile Thr Ala Ser Val Asp Gly Lys Ile Glu Arg Val
1               5                   10

<210> SEQ ID NO 17
<211> LENGTH: 54
<212> TYPE: DNA
<213> ORGANISM: Corynebacterium glutamicum

<400> SEQUENCE: 17
gtgactgcta tcacccttgg cggtctcttg ttgaaaggaa taattactct agtg              54

<210> SEQ ID NO 18
<211> LENGTH: 18
<212> TYPE: PRT
<213> ORGANISM: Corynebacterium glutamicum

<400> SEQUENCE: 18

Met Thr Ala Ile Thr Leu Gly Gly Leu Leu Leu Lys Gly Ile Ile Thr
1               5                   10                  15

Leu Val

<210> SEQ ID NO 19
<211> LENGTH: 1140
<212> TYPE: PRT
<213> ORGANISM: Corynebacterium glutamicum

<400> SEQUENCE: 19

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

-continued

```
Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590
```

-continued

```
Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
    755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
    915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe  Phe Tyr Gly Leu Val  Glu Gly Arg
    995                  1000                 1005

Glu Thr  Leu Ile Arg Leu Pro  Asp Val Arg Thr Pro  Leu Leu Val
```

-continued

```
                1010                    1015                    1020
Arg Leu Asp Ala Ile Ser Glu Pro Asp Asp Lys Gly Met Arg Asn
    1025                    1030                    1035

Val Val Ala Asn Val Asn Gly Gln Ile Arg Pro Met Arg Val Arg
    1040                    1045                    1050

Asp Arg Ser Val Glu Ser Val Thr Ala Thr Ala Glu Lys Ala Asp
    1055                    1060                    1065

Ser Ser Asn Lys Gly His Val Ala Ala Pro Phe Ala Gly Val Val
    1070                    1075                    1080

Thr Val Thr Val Ala Glu Gly Asp Glu Val Lys Ala Gly Asp Ala
    1085                    1090                    1095

Val Ala Ile Ile Glu Ala Met Lys Met Glu Ala Thr Ile Thr Ala
    1100                    1105                    1110

Ser Val Asp Gly Lys Ile Asp Arg Val Val Pro Ala Ala Thr
    1115                    1120                    1125

Lys Val Glu Gly Gly Asp Leu Ile Val Val Val Ser
    1130                    1135                    1140
```

What is claimed is:

1. A method of producing an amino acid, comprising:
   a) culturing a recombinant cell in a suitable media, wherein said recombinant cell comprises a vector comprising an isolated or purified nucleic acid molecule comprising a nucleotide sequence selected from the group consisting of:
   1) the nucleotide sequence encoding amino acids 1 to 1157 of SEQ ID NO: 2;
   2) a nucleotide sequence encoding the amino acid sequence encoded by the DNA plasmid encoding feedback-resistant pyruvate carboxylase enzyme, said plasmid contained in Deposit Number NRRL B-30293;
   3) a nucleotide sequence encoding a pyruvate carboxylase enzyme desensitized to feedback inhibition by aspartic acid, said enzyme having an amino acid sequence that differs from SEQ ID NO: 19 by at least one but not more than six mutations, said at least one, but no more than six mutations selected from the group consisting of:
      i) glutamic acid at position 153 is replaced with an aspartic acid,
      ii) alanine at position 182 is replaced with a serine,
      iii) alanine at position 206 is replaced with a serine,
      iv) histidine at position 227 is replaced with an arginine,
      v) alanine at position 455 is replaced with a glycine, and
      vi) aspartic acid at position 1120 is replaced with a glutamic acid; and
   4) a nucleotide sequence at least 95% identical to SEQ ID NO: 1 and which codes for a pyruvate carboxylase enzyme desensitized to feedback inhibition by aspartic acid, wherein said pyruvate carboxylase enzyme contains at least six mutations to SEQ ID NO: 19, wherein said at least six mutations to SEQ ID NO: 19 include:
      i) glutamic acid at position 153 is replaced with an aspartic acid,
      ii) alanine at position 182 is replaced with a serine,
      iii) alanine at position 206 is replaced with a serine,
      iv) histidine at position 227 is replaced with an arginine,
      v) alanine at position 455 is replaced with a glycine, and
      vi) aspartic acid at position 1120 is replaced with a glutamic acid; and
   b) separating said amino acid from said medium.

2. The method of claim 1, wherein said amino acid is selected from the group consisting of L-lysine, L-threonine, L-methionine, L-isoleucine, L-glutamic acid, L-arginine and L-proline.

3. The method of claim 2, wherein said amino acid is L-lysine.

4. A method of producing an amino acid, comprising:
   a) culturing a recombinant cell in a suitable medium, wherein said recombinant cell is a *Corynebacterium glutamicum* cell that comprises a feedback-resistant pyruvate carboxylase gene that has replaced the wild-type pyruvate carboxylase gene by a method comprising the steps of:
      A) replacing a genomic copy of said wild-type pyruvate carboxylase gene with a selectable marker gene through homologous recombination to form a first recombinant strain; and
      B) replacing said selectable marker gene of step (a) in said first recombinant strain with said feedback-resistant pyruvate carboxylase gene through homologous recombination to form a second recombinant strain;
   wherein said homologous recombination in steps (A) and (B) occurs between said host cell and a vector comprising an isolated or purified nucleic acid molecule comprising a nucleotide sequence selected from the group consisting of:
   1) the nucleotide sequence encoding amino acids 1 to 1157 of SEQ ID NO: 2;
   2) a nucleotide sequence encoding the amino acid sequence encoded by the DNA plasmid encoding feedback-resistant pyruvate carboxylase enzyme, said plasmid contained in Deposit Number NRRL B-30293;

3) a nucleotide sequence encoding a pyruvate carboxylase enzyme desensitized to feedback inhibition by aspartic acid, said enzyme having an amino acid sequence that differs from SEQ ID NO: 19 by at least one but not more than six mutations, said at least one, but no more than six mutations selected from the group consisting of:
   i) glutamic acid at position 153 is replaced with an aspartic acid,
   ii) alanine at position 182 is replaced with a serine,
   iii) alanine at position 206 is replaced with a serine,
   iv) histidine at position 227 is replaced with an arginine,
   v) alanine at position 455 is replaced with a glycine, and
   vi) aspartic acid at position 1120 is replaced with a glutamic acid; and 4) a nucleotide sequence at least 95% identical to SEQ ID NO: 1 and which codes for a pyruvate carboxylase enzyme desensitized to feedback inhibition by aspartic acid, wherein said pyruvate carboxylase enzyme contains at least six mutations to SEQ ID NO: 19, wherein said at least six mutations to SEQ ID NO: 19 include:
   i) glutamic acid at position 153 is replaced with an aspartic acid,
   ii) alanine at position 182 is replaced with a serine,
   iii) alanine at position 206 is replaced with a serine,
   iv) histidine at position 227 is replaced with an arginine,
   v) alanine at position 455 is replaced with a glycine, and
   vi) aspartic acid at position 1120 is replaced with a glutamic acid; and b) separating said amino acid from said medium.

5. The method of claim 4, wherein said amino acid is selected from the group consisting of: L-lysine, L-threonine, L-methionine, L-isoleucine, L-glutamic acid, L-arginine and L-proline.

6. The method of claim 5, wherein said amino acid is L-lysine.

* * * * *